United States Patent
Liu et al.

(10) Patent No.: US 10,793,543 B2
(45) Date of Patent: Oct. 6, 2020

(54) SELECTIVE C-KIT KINASE INHIBITOR

(71) Applicants: PRECEDO PHARMACEUTICALS CO., LTD, Hefei, Anhui (CN); HEFEI GRACEVO BIO-MEDICINE CO., LTD, Hefei, Anhui (CN)

(72) Inventors: Qingsong Liu, Anhui (CN); Jing Liu, Anhui (CN); Qiang Wang, Anhui (CN); Beilei Wang, Anhui (CN); Feiyang Liu, Anhui (CN); Shuang Qi, Anhui (CN); Ziping Qi, Anhui (CN); Fengming Zou, Anhui (CN); Cheng Chen, Anhui (CN); Wenchao Wang, Anhui (CN); Chen Hu, Anhui (CN); Xiaochuan Liu, Anhui (CN); Wei Wang, Anhui (CN); Aoli Wang, Anhui (CN); Li Wang, Anhui (CN); Zhenquan Hu, Anhui (CN); Tao Ren, Anhui (CN)

(73) Assignees: PRECEDO PHARMACEUTICALS CO., LTD, Hefei, Annui (CN); HEFEI GRACEVO BIO-MEDICINE CO., LTD, Hefei, Anhui (CN)

( * ) Notice: Subject to any disclaimer, the term of this patent is extended or adjusted under 35 U.S.C. 154(b) by 0 days.

(21) Appl. No.: 16/089,547

(22) PCT Filed: Mar. 28, 2017

(86) PCT No.: PCT/CN2017/078437
§ 371 (c)(1),
(2) Date: Sep. 28, 2018

(87) PCT Pub. No.: WO2017/167182
PCT Pub. Date: Oct. 5, 2017

(65) Prior Publication Data
US 2019/0084960 A1 Mar. 21, 2019

(30) Foreign Application Priority Data
Apr. 1, 2016 (CN) .......................... 2016 1 0210424

(51) Int. Cl.
| | |
|---|---|
| C07D 401/06 | (2006.01) |
| C07D 401/14 | (2006.01) |
| A61K 31/454 | (2006.01) |
| A61K 31/4545 | (2006.01) |
| C07D 409/14 | (2006.01) |
| C07D 211/44 | (2006.01) |
| C07D 413/14 | (2006.01) |
| A61K 31/45 | (2006.01) |
| C07D 413/04 | (2006.01) |
| C07D 401/04 | (2006.01) |
| A61P 35/00 | (2006.01) |
| A61K 31/445 | (2006.01) |
| C07D 413/06 | (2006.01) |

(52) U.S. Cl.
CPC .......... *C07D 401/06* (2013.01); *A61K 31/445* (2013.01); *A61K 31/45* (2013.01); *A61K 31/454* (2013.01); *A61K 31/4545* (2013.01); *A61P 35/00* (2018.01); *C07D 211/44* (2013.01); *C07D 401/04* (2013.01); *C07D 401/14* (2013.01); *C07D 409/14* (2013.01); *C07D 413/04* (2013.01); *C07D 413/06* (2013.01); *C07D 413/14* (2013.01)

(58) Field of Classification Search
CPC .................................................... C07D 401/06
USPC ......................................... 546/194; 514/318
See application file for complete search history.

(56) References Cited

FOREIGN PATENT DOCUMENTS

| | | |
|---|---|---|
| CN | 101291938 A | 10/2008 |
| CN | 101528744 A | 9/2009 |

(Continued)

OTHER PUBLICATIONS

Yu et al., "Physical characterization of, etc.," PSTT, vl. 1(3), 118-127). (Year: 1998).*

(Continued)

*Primary Examiner* — Patricia L Morris
(74) *Attorney, Agent, or Firm* — Scully, Scott, Murphy & Presser, P.C.

(57) ABSTRACT

The present invention provides a compound represented by formula (I), or a pharmaceutically acceptable salt, a solvate, an ester, an acid, a metabolite or a prodrug thereof. The compound itself in the present invention or in combination with at least one therapeutic agent can be used for preventing or treating diseases, disorders or symptoms caused by the adjustment of the activity of tyrosine kinase C-KIT, or affected by the activity of the tyrosine kinase C-KIT or involving in the activity of the tyrosine kinase C-KIT, especially cancers or other cell proliferation diseases.

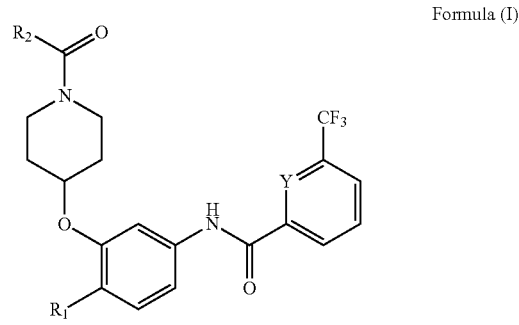

Formula (I)

8 Claims, 5 Drawing Sheets

(56) References Cited

FOREIGN PATENT DOCUMENTS

| | | |
|---|---|---|
| CN | 104844566 A | 8/2015 |
| WO | 2008/124393 A1 | 10/2008 |

OTHER PUBLICATIONS

Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26, (Year: 2001).*
Guillory (in Brittain ed.), "Polymorphism in Pharmaceutical Solids.," NY: Marcel Dekker, Inc., 1-2, 125-181, 183-226. (Year: 1999).*
Ettnnayer et al., "Lessons Learned, etc.," J. Med. Chem., 47(10): 2393-2404. (Year: 2004).*
Stella, "Prodrugs as therapeutics", Expert Opin. Ther. Patents, 14(3): 277-280. (Year: 2004).*
Testa, "Prodrug Research, etc.," Biochemical Pharmacology, 68:2097-2106 (Year: 2004).*
Wolff, ed., Burger's Medicinal Chemistry and Drug Discovery, 5th edition, NY: John Wiley & Sons, 1996, vol. 1, pp. 949-976.*
Bundgaard, Design of Prodrugs, Chapter 1, p. 1. (Year: 1985).*
Silverman, Prodrugs and Drug Delivery Systems, The Organic Chemistry of Drug Design and Drug Action, Chapter 8, pp. 352-400. (Year: 1992).*
Banker et al., Prodrugs, Modern Pharmaceutics, 3rd edition, Revised and Expanded, pp. 451 and 596. (Year: 1986).*
Johnson et al., Relationships between drug activity in NCI preclinical in vitro and in vivo models and early clinical trials, British Journal of Cancer (2001) 64(10): 1424-1431.*
Lodish et al., "Endocrine side, etc.," Endocrine-Related Cancer (2010) 17, R233-R244.*
Ouaissi et al., "Rationale for Possible, etc.," Journal of Biomedicine and Biotechnology, 2011, Article: ID 315939, 1-8.*
Golub et al, Science, vol. 286, Oct. 15, 1999, pp. 531-537.*
LeRoith et al., The insulin-like growth factor system and cancer, Cancer Letters, 195, pp. 127-137 (2003).*
Simone, Oncology:Introduction, Cecil Textbook of Medicine, ed Bennett et al. W.B.Saunders Co. 20th ed, vol. 1, 1996, pp. 1004-1010.*
Robinson, Medical Therapy of Inflammatory Bowel Disease for the 21st century, Eur. J. Surg. 164, Suppl. 582, pp. 90-98, (1998).*
Gura, Systems for identifying New Drugs Are Often Faulty, Cancer Models, Science, vol. 278, No. 5340, pp. 1041-1042, Nov. 1997.*
Gambacorti-Passerini C. et al., "Corrigendum: In Reply to 'Cardiotoxicity of the Cancer Therapeutic Agent Imatinib Mesylate'", Nature Medicine 13(1):13-14 (Jan. 2007).
Kerkelä R. et al., "Cardiotoxicity of the Cancer Therapeutic Agent Imatinib Mesylate", Nature Medicine 12 (8):908-916 (Aug. 2006).
Perik P.J. et al., "Results of Plasma N-Terminal Pro B-Type Natriuretic Peptide and Cardiac Troponin Monitoring in GIST Patients Do Not Support the Existence of Imatinib-Induced Cardiotoxicity", Annals of Oncology 19:359-361 (2008).
Wang Q. et al., "Discovery of N-(3-((1-Isonicotinoylpiperidin-4-yl)Oxy)-4-Methylphenyl)-3-(Trifluoromethyl) Benzamide (CHMFL-KIT-110) as a Selective, Potent, and Orally Available Type II c-KIT Kinase Inhibitor for Gastrointestinal Stromal Tumors (GISTs)", J. Med. Chem. 59:3964-3979 (Apr. 2016).
International Search Report dated Jul. 3, 2017 received in International Application No. PCT/CN2017/078437.

* cited by examiner a b a. Result of effect on animal models of GIST-T1 tumor b. Result of effect on animal models of GIST-882 tumor Animal models of GIST-T1 tumor c Animal models of GIST-882 tumor d e f

SELECTIVE C-KIT KINASE INHIBITOR

FIELD OF THE INVENTION

The present application relates to a compound used as a selective inhibitor of C-KIT kinase, a pharmaceutical composition comprising such compound, as well as a method and use for inhibiting the activity of C-KIT kinase by using such compound or composition.

BACKGROUND OF THE INVENTION

C-KIT is a proto-oncogene, a cytoplasmic retroviral homologue of HZ4 feline sarcoma virus, located on chromosome 4, 4q11-12. It encodes a transmembrane glycoprotein with a relative molecular mass of 145 kD, a member which belongs to the receptor tyrosine kinase family. The C-KIT receptor is divided into three parts: the extramembranous region, the transmembrane region and the cytoplasmic region. Abnormal expression of C-KIT is closely related to tumorigenesis. C-KIT is highly expressed in many malignant tumors, including gastrointestinal stromal tumor, prostate cancer, germ cell tumor, breast cancer, and small cell lung cancer, and the like. The receptor tyrosine kinase C-KIT (also known as CD117) is a class of transmembrane receptor protein with tyrosine kinase activity encoded by the retroviral proto-oncogene C-KIT, and constitutes a type III receptor tyrosine kinase superfamily together with platelet-derived growth factor receptor (PDGFR), macrophage colony-stimulating factor-1 receptor (CSF-1R) and Fms-like tyrosine kinase receptor 3 (FLT3). The receptor tyrosine kinase C-KIT plays an important role in the process of development, as well as invasion, migration and recurrence of the tumor. Inhibition of C-KIT-mediated signaling pathway to achieve tumor therapy has become a hot spot in tumor therapy in recent years. Therefore, C-KIT is one of the hot targets for tumor molecular targeted therapy.

Gastrointestinal stromal tumor (GIST) is a common tumor disease in the human digestive system. The concept of gastrointestinal stromal tumor was first proposed by Mazur and Clark in 1983. The pathological features of gastrointestinal stromal tumor are characterized by the abnormal appearance of smooth muscle and neurogenic gastrointestinal tumors. The incidence of gastrointestinal stromal tumor is only about between 10 and 20 cases per million (about 20,000 to 30,000 new cases of GIST in China each year), however, 67% of gastrointestinal stromal tumors are malignant. Gastrointestinal stromal tumor occurs mostly in middle-aged and elderly people, mainly in the 50-65 demographic, and there is no significant difference in the incidence between male and female. According to statistics, about 60-70% of gastrointestinal stromal tumors occur in the stomach, 20-30% occur in the small intestine, and about 10% occur in the esophagus, rectum, and colon.

The immunohistochemical diagnosis of gastrointestinal stromal tumor is characterized by the positive cell surface antigen CD117 (C-KIT protein), which is widely expressed on the cell surface of and in the cytoplasm of gastrointestinal stromal tumor, but not expressed in all non-gastrointestinal stromal tumor. The high sensitivity and specificity of CD117 make it a diagnostic indicator of gastrointestinal stromal tumor. For the treatment of gastrointestinal stromal tumor, in addition to surgery, the recent developed inhibitors targeting kinase C-KIT has become another important means for the treatment of gastrointestinal stromal tumor. At present, imatinib, which targets C-KIT, is mainly used for the initial treatment of gastrointestinal stromal tumor. However, imatinib has potential cardiotoxicity due to inhibition of the kinase Bcr-Abl, and some patients develop severe cardiotoxicity after taking imatinib (Kerkelä, R. et al., Cardiotoxicity of the cancer therapeutic agent imatinib mesylate, Nat. Med. 2006, 12, 908-916; Perik, P. J. et al., Results of plasma n-terminal pro b-type natriuretic peptide and cardiac troponin monitoring in gist patients do not support the existence of imatinib-induced cardiotoxicity, Ann. Oncol. 2008, 19, 359-361; Gianantonio, R. et al., In reply to 'cardiotoxicity of the cancer therapeutic agent imatinib mesylate', Nat. Med. 2007, 13, 13-4).

At the same time, another problem of the treatment with imatinib is that the patients develop resistance to the drug. According to statistics, the incidence of resistance to imatinib can be as high as 63% (including primary resistance and secondary resistance). Studies have found that imatinib resistance in patients with gastrointestinal stromal tumor is associated with mutations in the C-KIT gene, which leads to the continuous activation of tyrosine kinase activity, thereby leading to out of control of cell proliferation. Mutations in the C-KIT gene occur mostly in exons 11, 9, 13, and 17, and mutations in the C-KIT gene predict the tumors with a high degree of malignancy.

Therefore, the researchers desire to be able to develop a highly selective C-KIT kinase inhibitor to eliminate the potential risk of cardiotoxicity, and meantime, the researchers also desire to be able to develop a targeted drug, which exhibits inhibition not only to wild-type C-KIT gene, but also to the mutant C-KIT genes, to replace imatinib, thereby solving the problem of drug resistance.

SUMMARY OF THE INVENTION

The present invention provides a selective inhibitor of C-KIT kinase, comprising a compound of formula (I), or a pharmaceutically acceptable salt, solvate, ester, acid, metabolite or prodrug thereof:

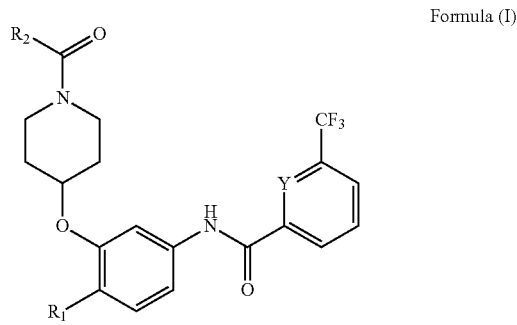

Formula (I)

wherein, Y is selected from the group consisting of CH and N; $R_1$ is selected from the group consisting of H, $C_{1-6}$ alkyl, $C_{1-6}$ alkoxy and halogen; $R_2$ is selected from the group consisting of $C_{1-6}$ alkyl, $C_{2-6}$ alkenyl, phenyl optionally substituted with $R_3$, and heteroaryl optionally substituted with $R_3$; $R_3$ is selected from the group consisting of $C_{1-6}$ alkyl and $C_{1-6}$ alkylamino.

In preferred embodiments, Y is CH.

In further preferred embodiments, $R_1$ is selected from the group consisting of H, methyl, methoxy, and chloro, especially methyl.

In yet preferred embodiments, $R_2$ is selected from the group consisting of ethyl, vinyl, phenyl, pyridinyl, isoxazolyl, thienyl, and imidazolyl, wherein phenyl, pyridinyl, isoxazolyl, thienyl, and imidazolyl are optionally substituted with methyl or dimethylamino. In particular, $R_2$ further preferably is 2-pyridinyl, 3-pyridinyl or 4-pyridinyl, most preferably is 4-pyridinyl.

The present invention further relates to a pharmaceutical composition comprising the above compound, or a pharmaceutically acceptable salt, solvate, ester, acid, metabolite or prodrug thereof, as well as a method and use of such compound and pharmaceutical composition for inhibiting the activity of tyrosine kinase C-KIT (wild-type or various mutants or the combination thereof) and/or PDGFR (wild-type or various mutants or the combination thereof), and a method and use for the treatment, prevention or amelioration of a disease, disorder, or condition, which is modulated or otherwise affected by tyrosine kinase C-KIT (wild-type or various mutants or the combination thereof) activity, or in which tyrosine kinase C-KIT (wild-type or various mutants or the combination thereof) activity is implicated.

DESCRIPTION OF THE FIGURES

FIG. 5 illustrates the experimental results obtained by treating mouse tumor models of human gastrointestinal stromal tumor cells GIST-T1 cells and human gastrointestinal stromal tumor cells GIST-882 cells with different concentrations of Compound 4 and imatinib, solvent control, respectively, wherein FIG. 5a illustrates the changes in the average size of tumors in different treatment groups over time, in the mouse tumor models of human gastrointestinal stromal tumor cells GIST-T1 cells; FIG. 5b illustrates the changes in the average size of tumors, in different treatment groups over time in the mouse tumor models of human gastrointestinal stromal tumor cells GIST-882 cells; FIG. 5c illustrates the changes in the average relative body weight of the mice (percentage calculated based on the weight of the mouse at the start of the experiment) in different treatment groups over time, in the mouse tumor models of GIST-T1 cells; FIG. 5d illustrates the changes in the average relative body weight of the mice (percentage calculated based on the weight of the mouse at the start of the experiment) in different treatment groups over time, in the mouse tumor models of GIST-882 cells; FIG. 5e illustrates the tumor inhibition rate calculated after 28 days from treating the mice with different concentrations of Compound 4, imatinib, and solvent, in the mouse tumor models of GIST-T1 cells; FIG. 5f illustrates the tumor inhibition rate calculated after 21 days from treating the mice with different concentrations of Compound 4, imatinib, and solvent, in the mouse tumor models of GIST-882 cells.

DETAILED DESCRIPTION OF THE INVENTION

Terminology

Figure 1:
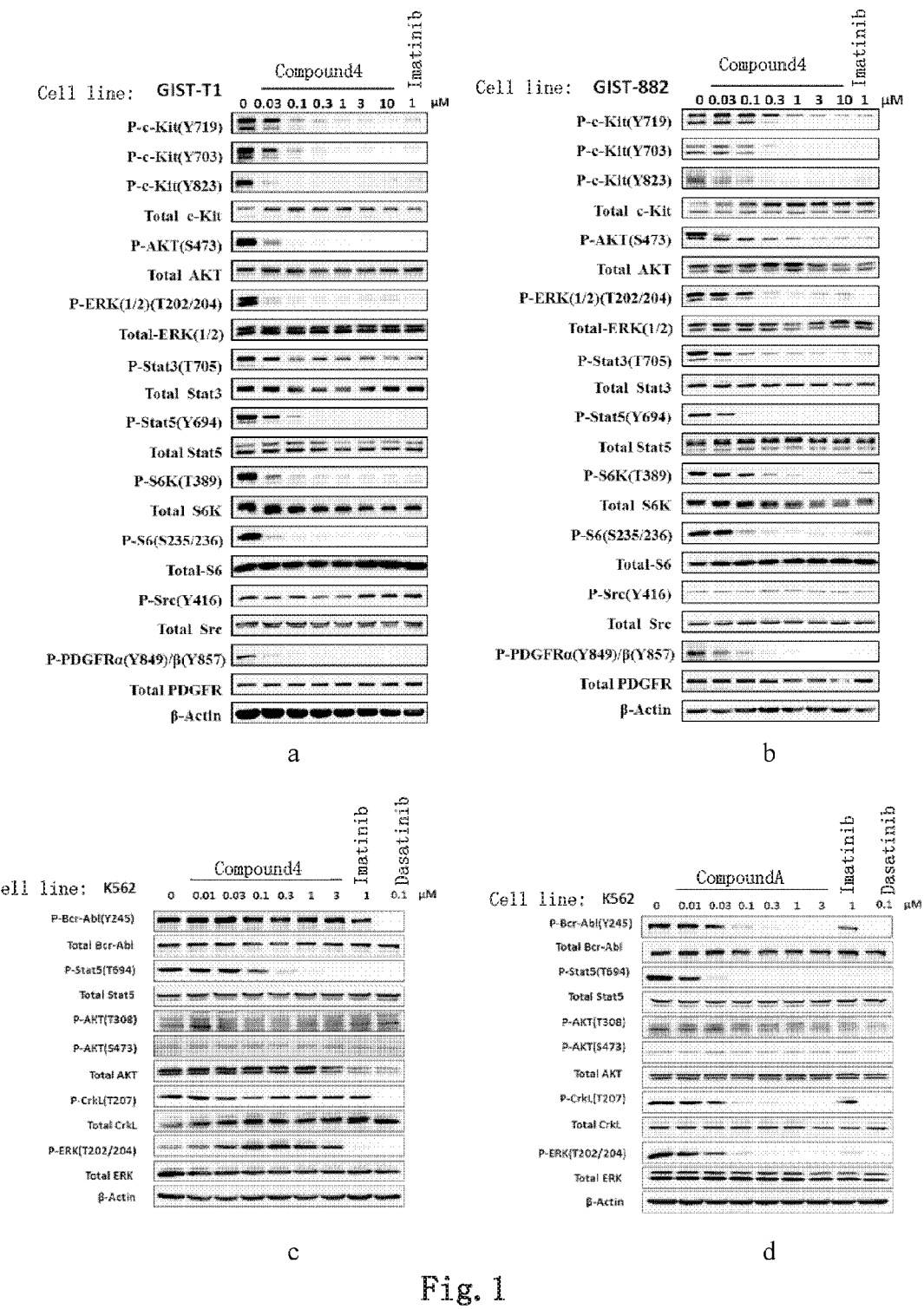
FIG. 1a illustrates the effects of Compound 4 and imatinib on the proteins in the signaling pathway in human gastrointestinal stromal tumor cells GIST-T1.
FIG. 1b illustrates the effects of Compound 4 and imatinib on the proteins in the signaling pathway in human gastrointestinal stromal tumor cells GIST-882.
FIG. 1c illustrates the effects of Compound 4, imatinib and dasatinib on the proteins in the signaling pathway in chronic myelogenous leukemia cells K562.
FIG. 1d illustrates the effects of comparative compound A, imatinib and dasatinib on the proteins in the signaling pathway in chronic myelogenous leukemia cells K562.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the present invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the present invention, the alkyl group is preferable a "lower alkyl" having 1 to 8 carbon atoms. Typical alkyl groups include, but are not limited to, methyl, ethyl, propyl, isopropyl, butyl, isobutyl, tertiary butyl, pentyl, hexyl, and the like.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "halo" or "halogen" means fluoro, chloro, bromo and iodo.

The term "amino" refers to an —$NH_2$ group.

The term "alkylamino" refers to an amino substituent which is further substituted with one or two alkyl groups, specifically the group —NRR', wherein R and R' are each independently selected from the group consisting of hydrogen or lower alkyl, with the proviso that —NRR' is not —$NH_2$.

The term "carbonyl" is an organic functional group (C=O) formed by carbon atom and oxygen atom through a double bond linkage.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

The term "optionally substituted" or "substituted" means that the referenced group may be substituted with one or more additional group(s) which are each independently selected from alkyl, cycloalkyl, aryl, heteroaryl, hydroxy, alkoxy, cyano, halo, amide, nitro, haloalkyl, amino protecting group, and the like.

The term "tyrosine protein kinase (TPK)" used herein is a type of kinases that catalyze the transfer of the γ-phosphate from adenosine triphosphate (ATP) to tyrosine residue on proteins and that is capable of catalyzing the phosphorylation of tyrosine residue of various protein substrates, and thus have an important effect on cell growth, proliferation and differentiation.

The terms "inhibits", "inhibiting", or "inhibitor" of a kinase, as used herein, refer to inhibition of phosphotransferase activity.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being bound by a selective binding compound. In certain embodiments, the target protein is tyrosine kinase C-KIT (wild-type or various mutants or the combination thereof), and/or PDGFR (wild-type or various mutants or the combination thereof). In certain embodiments, the target protein is wild-type tyrosine kinase C-KIT (wild-type or various mutants or the combination thereof). In certain embodiments, the target protein is wild-type tyrosine kinase C-KIT.

As used herein, $GI_{50}$ refers to a drug concentration required for growth inhibition of 50% cells, i.e., a drug concentration at which the growth of 50% cells (such as cancer cells) can be inhibited or controlled by the drug.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

In the present application, a specific gene or a protein encoded thereby is represented by the same letter combination symbol (an Arabic numeral is also used in some symbols), regardless of whether the letter is uppercase or lowercase. For example, the KIT, and/or Kit, and/or CKIT, and/or C-KIT, and/or kit used herein refers to the KIT gene and/or KIT protein; BCR-ABL, and/or Bcr-Abl, and/or bcr-abl, and/or BCR/ABL, and/or BCR/ABL1, and/or Bcr/Abl1, and/or bcr/abl1 used herein refers to the Bcr-Abl gene and/or Bcr-Abl protein. Also, those skilled in the art can readily determine, based on the context of the present application, whether the letter symbol in a particular expression refers to a gene or a protein.

The Novel Kinase Inhibitor of the Present Invention

The present invention provides a selective inhibitor of C-KIT kinase, comprising a compound of formula (I), or a pharmaceutically acceptable salt, solvate, ester, acid, metabolite or prodrug thereof:

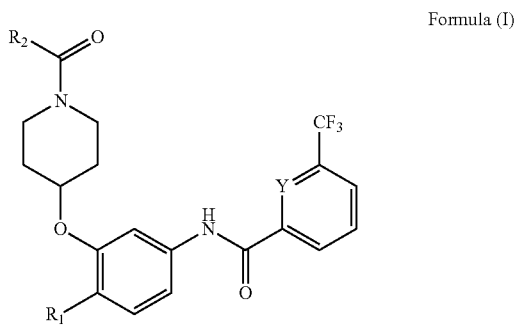

Formula (I)

wherein, Y is selected from the group consisting of CH and N; $R_1$ is selected from the group consisting of H, $C_{1-6}$ alkyl, $C_{1-6}$ alkoxy and halogen; $R_2$ is selected from the group consisting of $C_{1-6}$ alkyl, $C_{2-6}$ alkenyl, phenyl optionally substituted with $R_3$, and heteroaryl optionally substituted with $R_3$; $R_3$ is selected from the group consisting of $C_{1-6}$ alkyl and $C_{1-6}$ alkylamino.

In preferred embodiments, Y is CH.

In further preferred embodiments, $R_1$ is selected from the group consisting of H, methyl, methoxy, and chloro, especially methyl.

In yet preferred embodiments, $R_2$ is selected from the group consisting of ethyl, vinyl, phenyl, pyridinyl, isoxazolyl, thienyl, and imidazolyl, wherein phenyl, pyridinyl, isoxazolyl, thienyl, and imidazolyl are optionally substituted with methyl or dimethylamino. In particular, $R_2$ further preferably is 2-pyridinyl, 3-pyridinyl or 4-pyridinyl, most preferably is 4-pyridinyl.

The especially preferred compounds in the present invention include the compounds below:

| | | |
|---|---|---|
| 1 | 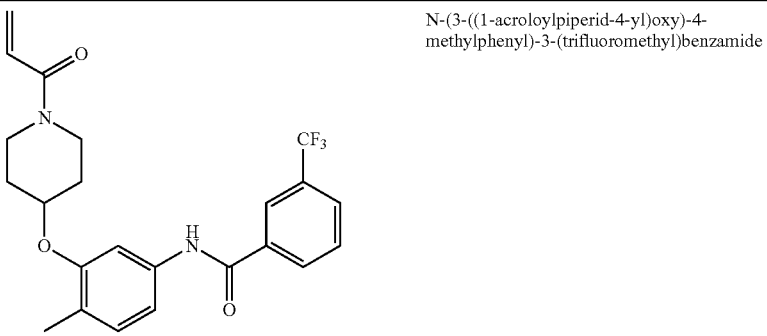<br>Compound 1 | N-(3-((1-acroloylpiperid-4-yl)oxy)-4-methylphenyl)-3-(trifluoromethyl)benzamide |
| 2 | 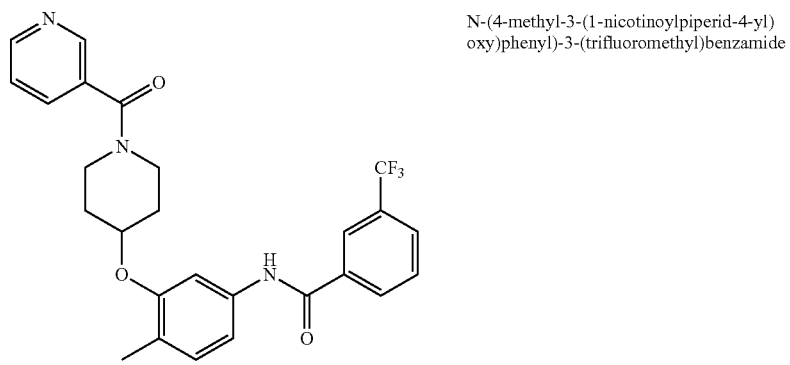<br>Compound 2 | N-(4-methyl-3-(1-nicotinoylpiperid-4-yl)oxy)phenyl)-3-(trifluoromethyl)benzamide |
| 3 | 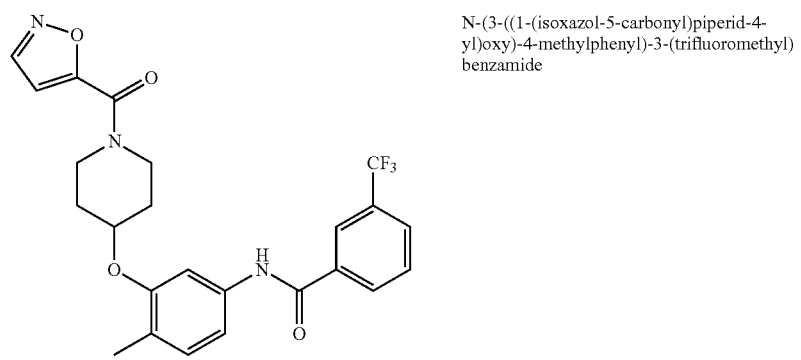<br>Compound 3 | N-(3-((1-(isoxazol-5-carbonyl)piperid-4-yl)oxy)-4-methylphenyl)-3-(trifluoromethyl)benzamide |
| 4 | 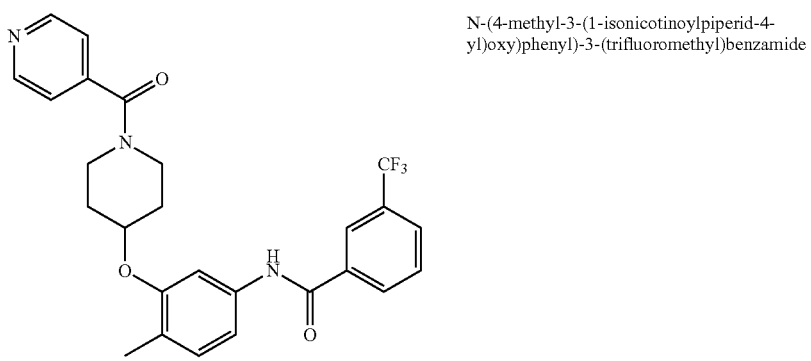<br>Compound 4 | N-(4-methyl-3-(1-isonicotinoylpiperid-4-yl)oxy)phenyl)-3-(trifluoromethyl)benzamide |

| | | |
|---|---|---|
| 5 | 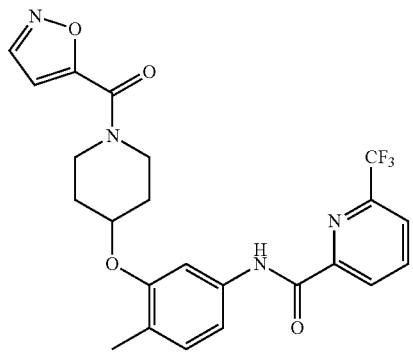 [SMILES: Cc1ccc(NC(=O)c2cccc(C(F)(F)F)n2)cc1OC1CCN(C(=O)c2ccno2)CC1]<br>Compound 5 | N-(3-((1-(isoxazol-5-carbonyl)piperid-4-yl)oxy)-4-methylphenyl)-6-(trifluoromethyl)picolinamide |
| 6 | 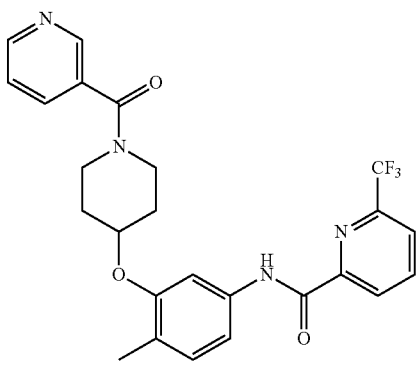<br>Compound 6 | N-(4-methyl-3-(1-nicotinoylpiperid-4-yl)oxy)phenyl)-6-(trifluoromethyl)picolinamide |
| 7 | 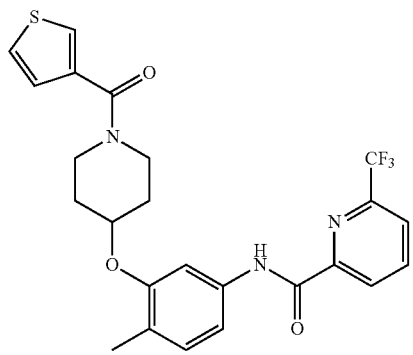 [SMILES: Cc1ccc(NC(=O)c2cccc(C(F)(F)F)n2)cc1OC1CCN(C(=O)c2ccsc2)CC1]<br>Compound 7 | N-(4-methyl-3-((1(thien-3-carbonyl)piperid-4-yl)oxy)phenyl)-6-(trifluoromethyl)picolinamide |
| 8 | 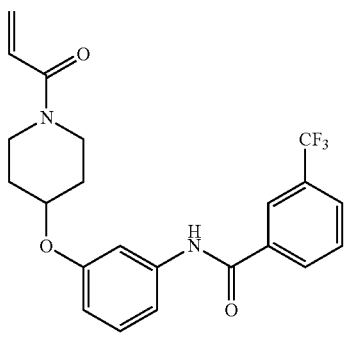 [SMILES: C=CC(=O)N1CCC(Oc2cccc(NC(=O)c3cccc(C(F)(F)F)c3)c2)CC1]<br>Compound 8 | N-(3-((1-acroloylpiperid-4-yl)oxy)phenyl)-3-(trifluoromethyl)benzamide |

-continued
| | | |
|---|---|---|
| 9 | 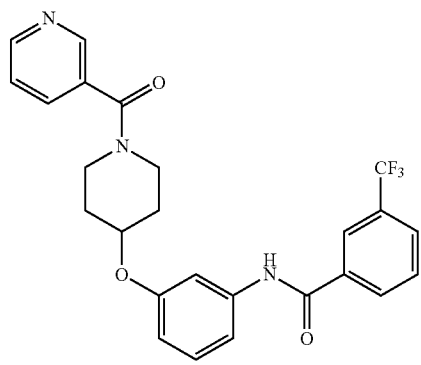 [SMILES: O=C(Nc1cccc(OC2CCN(C(=O)c3cccnc3)CC2)c1)c1cccc(C(F)(F)F)c1]<br>Compound 9 | N-(3-((nicotinoylpiperid-4-yl)oxy)phenyl)-3-(trifluoromethyl)benzamide |
| 10 | 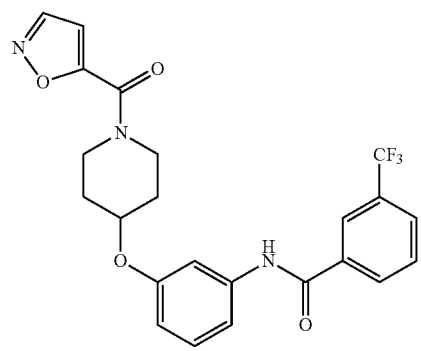 [SMILES: O=C(Nc1cccc(OC2CCN(C(=O)c3ccno3)CC2)c1)c1cccc(C(F)(F)F)c1]<br>Compound 10 | N-(3-((1-(isoxazol-5-carbonyl)piperid-4-yl)oxy)phenyl)-3-(trifluoromethyl)benzamide |
| 11 | 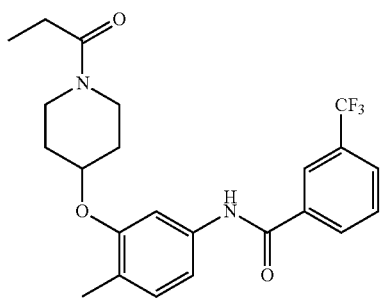 [SMILES: CCC(=O)N1CCC(Oc2cc(NC(=O)c3cccc(C(F)(F)F)c3)ccc2C)CC1]<br>Compound 11 | N-(3-((1-propionylpiperid-4-yl)oxy)-4-methylphenyl)-3-(trifluoromethyl)benzamide |
| 12 | 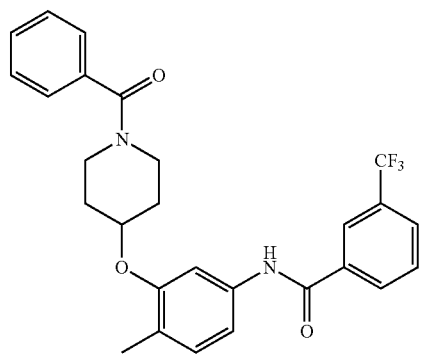<br>Compound 12 | N-(3-(1-benzoylpiperid-4-yl)oxy)-4-methylphenyl)-3-(trifluoromethyl)benzamide |

-continued
| 13 | 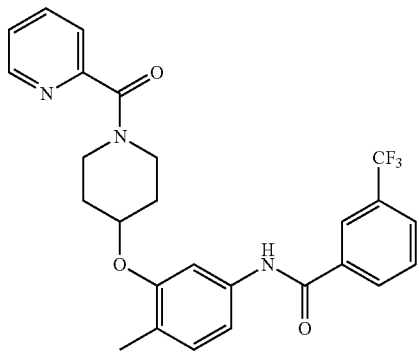
Compound 13 | N-(4-methyl-3-((1-pyridin-2-formylpiperid-4-yl)oxy)phenyl)-3-(trifluoromethyl) benzamide |
| --- | --- | --- |
| 14 | 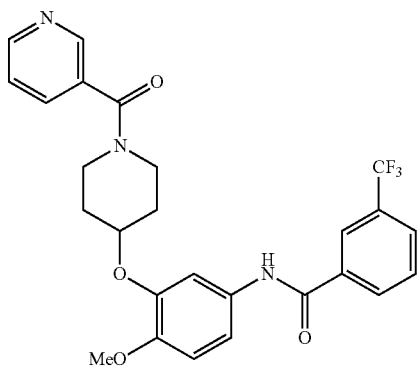 [SMILES: COc1ccc(NC(=O)c2cccc(C(F)(F)F)c2)cc1OC1CCN(C(=O)c2cccnc2)CC1]
Compound 14 | N-(4-methoxy-3-(1-nicotinoylpiperid-4-yl) oxy)phenyl)-3-(trifluoromethyl)-benzamide |
| 15 | 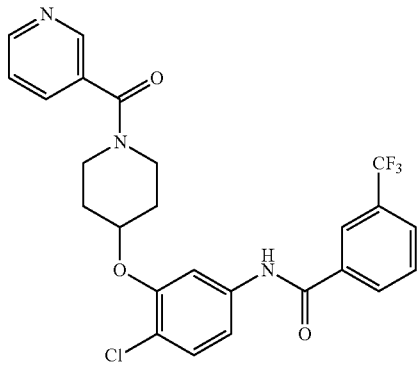 [SMILES: O=C(Nc1ccc(Cl)c(OC2CCN(C(=O)c3cccnc3)CC2)c1)c1cccc(C(F)(F)F)c1]
Compound 15 | N-(4-chloro-3-(1-nicotinoylpiperid-4-yl) oxy)phenyl)-3-(trifluoromethyl)-benzamide |
| 16 | 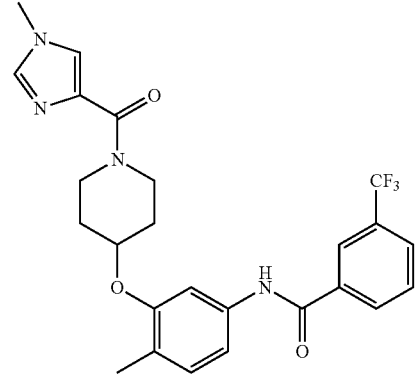 [SMILES: Cc1ccc(NC(=O)c2cccc(C(F)(F)F)c2)cc1OC1CCN(C(=O)c2cn(C)cn2)CC1]
Compound 16 | N-(4-methyl-3-((1-(1-methyl-1H-imidazol-4-carbonyl)piperid-4-yl)oxy)phenyl)-3-(trifluoromethyl)benzamide |

| | | |
|---|---|---|
| 17 | 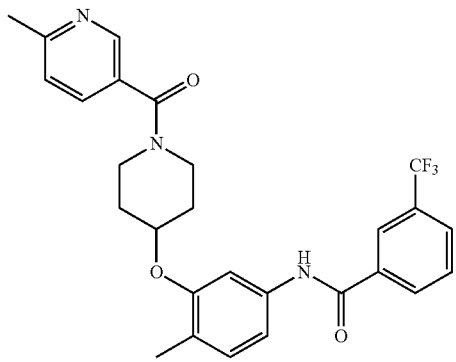 [SMILES: Cc1ccc(C(=O)N2CCC(Oc3cc(NC(=O)c4cccc(C(F)(F)F)c4)ccc3C)CC2)cn1]"Compound 17" | N-(4-methyl-3-((1-(2-methylnicotinoyl)piperid-4-yl)oxy)phenyl)-3-(trifluoromethyl)benzamide |
| 18 | 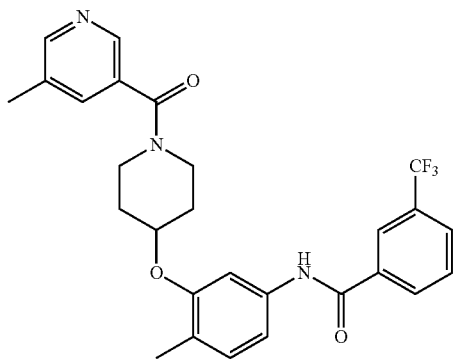 [SMILES: Cc1cncc(C(=O)N2CCC(Oc3cc(NC(=O)c4cccc(C(F)(F)F)c4)ccc3C)CC2)c1]"Compound 18" | N-(4-methyl-3-((1-(3-methylnicotinoyl)piperid-4-yl)oxy)phenyl)-3-(trifluoromethyl)benzamide |
| 19 | 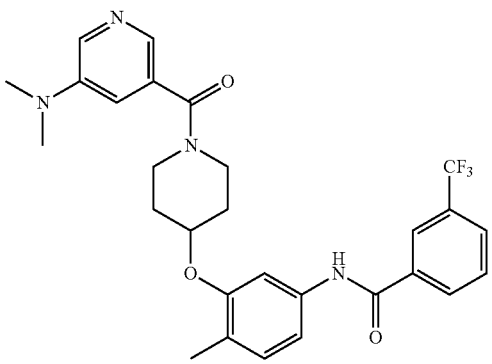 [SMILES: Cc1ccc(NC(=O)c2cccc(C(F)(F)F)c2)cc1OC1CCN(C(=O)c2cncc(N(C)C)c2)CC1]"Compound 19" | N-(3-((1-(3-(dimethylamino)nicotinoyl)piperid-4-yl)oxy)-4-methylphenyl)-3-(trifluoromethyl)benzamide |

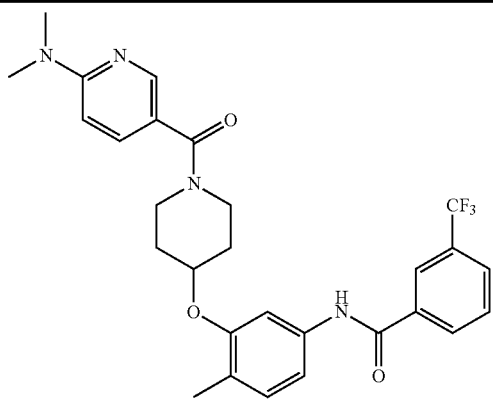

Compound 20 — N-(3-((1-(2-(dimethylamino)nicotinoyl)piperid-4-yl)oxy)-4-methylphenyl)-3-(trifluoromethyl)benzamide Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Described herein is a novel kinase inhibitor. The pharmaceutically acceptable salts, solvates, esters, acids, pharmaceutically active metabolites and prodrugs of these compounds are also described herein.

In additional or further embodiments, the compounds described herein are metabolized upon administration to an organism in need thereof to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2] oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) base addition salts formed when an acidic proton present in the parent compound either is replaced by a metal ion, e.g., an alkali metal ion (e.g. lithium, sodium, potassium), an alkaline earth metal ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a nonsolvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, microscopy, and element analysis. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention

The present application also provides a pharmaceutical composition comprising at least one compound of formula (I), or a pharmaceutically acceptable salt, solvate, ester, acid, pharmaceutically active metabolite or prodrug of the compound, and a pharmaceutically acceptable carrier or excipient, and optionally other therapeutic agents.

In the course of treatment, it may be used alone or in combination with one or more other therapeutic agents. The medicament comprising a compound of the present invention may be administered to a patient through at least one of injection, oral, inhalation, rectal and transdermal administration. Other therapeutic agents may be selected from the following: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be for example, but are not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In the embodiments of the present invention, when a patient is treated in accordance with the present invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

Use of Medicines of the Present Invention

The compound of formula (I), or a pharmaceutically acceptable salt, solvate, ester, acid, metabolite or prodrug thereof, or the pharmaceutical composition may be used for inhibiting the activity of tyrosine kinase C-KIT (wild-type or various mutants or the combination thereof) and/or PDGFR (wild-type or various mutants or the combination thereof). The compound of formula (I), or a pharmaceutically acceptable salt, solvate, ester, acid, metabolite or prodrug thereof, or the pharmaceutical composition may be used for the treatment, prevention or amelioration of one or more diseases selected from the group consisting of: solid tumors (including benign or especially malignant types), especially sarcoma, Gastrointestinal Stromal Tumor (GIST), colorectal cancer, Acute Myeloblastic Leukemia (AML), Chronic Myelogenous Leukemia (CML), neoplasia, thyroid carcinoma, systemic mastocytosis, eosinophilia syndrome, fibrosis, lupus erythematosus, graft versus host disease, neurofibromatosis, pulmonary hypertension, Alzheimer's disease, seminoma, dysgerminoma, mast cell tumors, lung cancer, bronchial carcinoma, testicular intraepithelial neoplasia, melanoma, breast cancer, neuroblastoma, papillary/follicular thyroid carcinoma, malignant lymphoma, non-Hodgkin's lymphoma, multiple endocrine neoplasia type 2, pheochromocytoma, thyroid carcinoma, parathyroid hyperplasia/adenoma, colon cancer, colorectal adenoma, ovarian cancer, prostate cancer, glioblastoma, brain tumor, malignant glioma, pancreatic cancer, malignant pleural endothelioma, hemangioblastoma, hemangioma, kidney cancer, liver cancer, adrenal carcinoma, bladder cancer, stomach cancer, rectal cancer, vaginal cancer, cervical cancer, endometrial cancer, multiple myeloma, neck and head tumors, as well as other proliferative conditions, or the like, or the combination thereof. It is especially preferred for the treatment of Gastrointestinal Stromal Tumor (GIST), colorectal cancer, Acute Myeloblastic Leukemia (AML), Chronic Myelogenous Leukemia (CML), thyroid carcinoma, or the like, or the combination thereof.

The compound of formula (I), or a pharmaceutically acceptable salt, solvate, ester, acid, metabolite or prodrug thereof, or the pharmaceutical composition may be used for the treatment, prevention or amelioration of the autoimmune disease selected from the group consisting of: arthritis, rheumatic arthritis, osteoarthritis, lupus, rheumatoid arthritis, inflammatory bowel disease, psoriatic arthritis, osteoarthritis, Still's disease, Juvenile arthritis, diabetes, myasthenia gravis, Hashimoto's thyroiditis, Ord's hyroiditis, Graves' disease, Sjögren's syndrome, multiple sclerosis, Guillain-Barré syndrome, acute disseminated encephalomyelitis, Addison's disease, Opsoclonus-Myoclonus-Ataxia, ankylosing spondylitis, antiphospholipid syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm-type autoimmune hemolytic anemia, Wegener's granulomatosis, psoriasis, alopecia universalis, Behcet's disease, chronic fatigue, Familial dysautonomia, endometriosis, interstitial cystitis, neuromyotonia, scleroderma or vulvodynia.

Preparation of the Compound

Compounds of formula (I) may be synthesized using standard synthetic techniques known to those of skill in the art or using methods known in the art in combination with methods described herein. In additions, solvents, temperatures and other reaction conditions presented herein may vary according to those of skill in the art. As a further guide the following synthetic methods may also be utilized.

The reactions can be employed in a linear sequence to provide the compounds described herein or they may be used to synthesize fragments which are subsequently joined by the methods described herein and/or known in the art.

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

A non-limiting example of a synthetic approach towards the preparation of compounds of formula (I) is shown in the following synthetic routes.

EXAMPLE 1

Synthesis of Compound 4

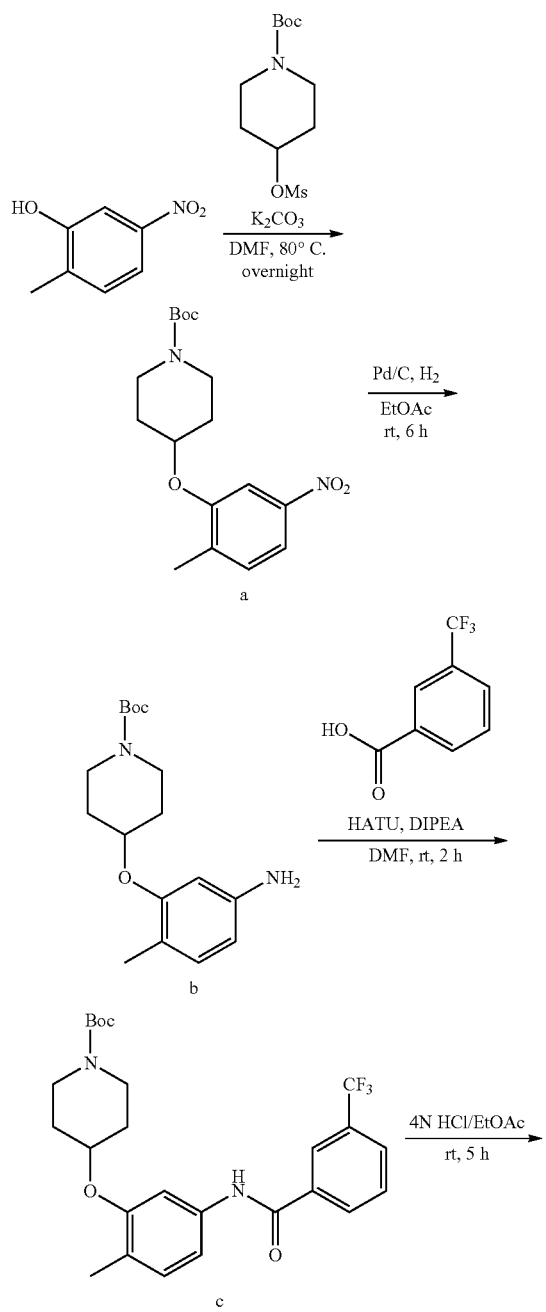

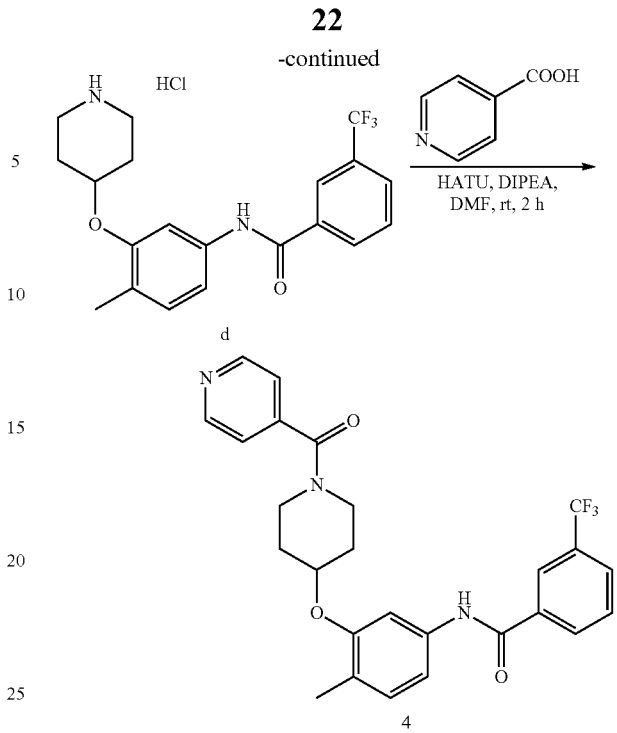

Synthesis of tert-butyl 4-(2-methyl-5-nitrophenoxy) piperidine-1-carboxylate Compound a 5 mmol of 2-methyl-5-nitrophenol, 6 mmol of 1-tert-butoxycarbonyl-4-methanesulfonyloxypiperidine and 10 mmol of anhydrous potassium carbonate were successively added to 15 ml of anhydrous N,N-dimethylformamide (DMF). The reaction system was allowed to react at 80° C. overnight, cooled to room temperature, and then extracted with ethyl acetate. The organic phases were combined and dried over anhydrous sodium sulfate. The solvent was removed by a rotary evaporator, and the crude product was separated on silica gel column to obtain a product of tert-butyl 4-(2-methyl-5-nitrophenoxy)piperidine-1-carboxylate compound a (yield: 89%). Exact Mass (calculated): 336.17; MS (ESI) m/z (M+Na)$^+$: 359.20.

Synthesis of tert-butyl 4-(2-methyl-5-aminophenoxy) piperidine-1-carboxylate Compound b 4 mmol tert-butyl 4-(2-methyl-5-nitrophenoxy) piperidine-1-carboxylate compound a was dissolved in 20 ml of ethyl acetate, then 0.05 equivalent of Pd/C (10%) was added. The system was reacted for 6 hours under a hydrogen atmosphere at atmospheric pressure. The reaction system was filtered with diatomaceous earth, and the filtrate was collected and the solvent was removed to obtain a product of tert-butyl 4-(2-methyl-5-aminophenoxy)piperidine-1-carboxylate compound b (yield: 96%). Exact Mass (calculated): 306.19; MS (ESI) m/z (M+Na)$^+$: 329.23.

Synthesis of tert-butyl 4-(2-methyl-5-(3-(trifluoromethyl)benzoylamino)phenoxy)piperidine-1-carboxylate Compound c 5 mmol of tert-butyl 4-(2-methyl-5-aminophenoxy) piperidine-1-carboxylate b, 5 mmol of 3-trifluoromethylbenzoic acid, 10 mmol of N,N-diisopropylethylamine (DIPEA) and 15 ml of anhydrous N,N-dimethylformamide (DMF) were successively added to a 50 ml round bottom flask, and 6 mmol of 2-(7-azobenzotriazole)-N,N,N',N'-tetramethylurea hexafluorophosphate (HATU) was added under stirring. The reaction system was reacted under stirring at room temperature for 2 hours. The reaction system was extracted with ethyl acetate and dried over anhydrous sodium sulfate. The solvent was removed by a rotary evaporator, and the crude product was separated on silica gel column to obtain a product of tert-butyl 4-(2-methyl-5-(3-(trifluoromethyl) benzoylamino)phenoxy)piperidine-1-carboxylate compound c (yield: 82%). Exact Mass (calculated): 478.20; MS (ESI) m/z (M+H)$^+$: 479.20.

Synthesis of N-(4-methyl-3-(piperid-4-yloxy)phenyl)-3-(trifluoromethyl)benzamide hydrochlorate Compound d 3 mmol of tert-butyl 4-(2-methyl-5-(3-(trifluoromethyl) benzoylamino)phenoxy)piperidine-1-formic acid compound c was placed in a 25 mL round bottom flask, 20 mL of 4N hydrochloric acid/ethyl acetate solution was added and stirred at room temperature for 5 h, suction filtered to give a solid, and the solid was washed with ethyl acetate, and dried to obtain a product of N-(4-methyl-3-(piperid-4-yloxy) phenyl)-3-(trifluoromethyebenzamide hydrochlorate compound d (yield: 76%). Exact Mass (calculated): 378.15; MS (ESI) m/z (M+H)$^+$: 379.15.

Synthesis of N-(4-methyl-3-(1-isonicotinoylpiperid-4-yl)oxy)phenyl)-3-(trifluoromethyl) benzamide Compound 4

0.05 mmol of N-(4-methyl-3-(piperid-4-yloxy)phenyl)-3-(trifluoromethyebenzamide hydrochlorate d, 0.05 mmol of isonicotinic acid, 0.1 mmol of N,N-diisopropylethylamine (DIPEA) and 1 ml of anhydrous N,N-dimethylformamide (DMF) were successively added to 5 mL round bottom flask, and 0.06 mmol of 2-(7-azobenzotriazole)-N,N,N',N'-tetramethylurea hexafluorophosphate (HATU) was added under stirring. The reaction system was reacted under stirring at room temperature for 2 hours. The reaction system was extracted with ethyl acetate and dried over anhydrous sodium sulfate. The solvent was removed by a rotary evaporator, and the crude product was separated on silica gel column to obtain a product of N-(4-methyl-3-(1-isonicotinoylpiperid-4-yl)oxy)phenyl)-3-(trifluoromethyl) benzamide compound 4 (yield: 67%).

$^1$H NMR (400 MHz, DMSO-d$_6$) δ 10.37 (s, 1H), 8.67 (s, 2H), 8.27 (s, 2H), 7.96 (d, J=6.8 Hz, 1H), 7.79-7.76 (m, 1H), 7.48 (s, 1H), 7.43 (s, 2H), 7.29 (d, J=8.0 Hz, 1H), 7.14 (d, J=7.6 Hz, 1H), 4.60 (s, 1H), 3.83-3.28 (m, 4H), 2.16 (s, 3H), 1.95 (s, 2H), 1.77 (s, 2H). Exact Mass (calculated): 483.17; MS (ESI) m/z (M+H)$^+$: 484.17.

Those skilled in the art may synthesize other preferred compounds of the present invention using suitable starting materials in accordance with known standard synthetic techniques in a manner similar to Example 1 above. Examples thereof were as shown in Table 1 below.

TABLE 1

Exemplary compounds of the present invention and its characterization data

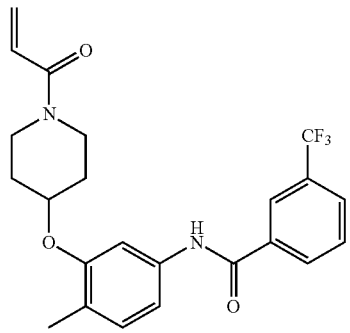 [SMILES: C=CC(=O)N1CCC(Oc2cc(NC(=O)c3cccc(C(F)(F)F)c3)ccc2C)CC1]

Compound 1

N-(3-((1-acroloylpiperid-4-yl)oxy)-4-methylphenyl)-3-(trifluoromethyl)benzamide

Exact Mass (calculated): 432.16; MS (ESI) m/z (M + 1)$^+$: 433.16.

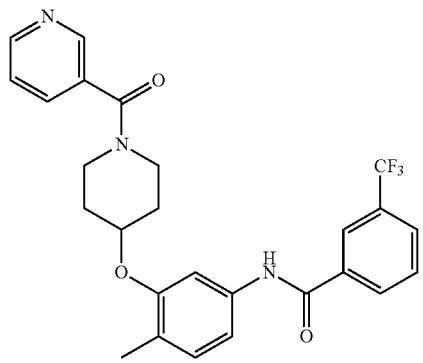 [SMILES: Cc1ccc(NC(=O)c2cccc(C(F)(F)F)c2)cc1OC1CCN(C(=O)c2cccnc2)CC1]

Compound 2

N-(4-methyl-3-(1-nicotinoylpiperid-4-yl)oxy)phenyl)-3-(trifluoromethyl)benzamide $^1$H NMR (400 MHz, DMSO) δ 10.39 (s, 1H), 8.65 (s, 2H), 8.27 (s, 2H), 7.87-7.78 (m, 3H), 7.48 (s, 2H), 7.30 (s, 1H), 7.14 (s, 1H), 4.61 (s, 1H), 3.86-3.36 (m, 3H), 2.16 (s, 3H), 2.02 (s, 2H), 1.79 (s, 2H). Exact Mass (calculated): 483.17; MS (ESI) m/z (M + 1)$^+$: 484.17.

TABLE 1-continued

Exemplary compounds of the present invention and its characterization data

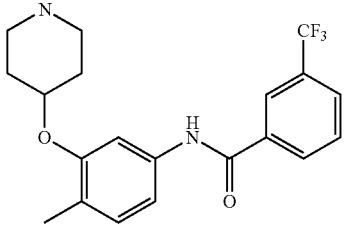

Compound 3

N-(3-((1-(isoxazol-5-carbonyl)piperid-4-yl)oxy)-4-methylphenyl)-3-(trifluoromethyl)benzamide Exact Mass (calculated): 473.15; MS (ESI) m/z (M + 1)$^+$: 474.15.

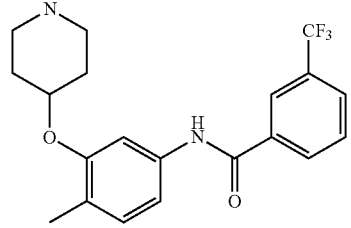

Compound 4

N-(4-methyl-3-(1-isonicotinoylpiperid-4-yl)oxy)phenyl)-3-(trifluoromethyl)benzamide Exact Mass (calculated): 483.17; MS (ESI) m/z (M + 1)$^+$: 484.17.

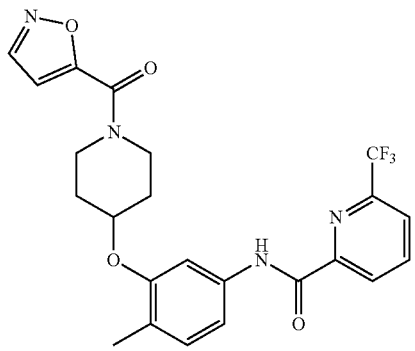 [SMILES: Cc1ccc(NC(=O)c2cccc(C(F)(F)F)n2)cc1OC1CCN(C(=O)c2ccno2)CC1]

Compound 5

N-(3-((1-(isoxazol-5-carbonyl)piperid-4-yl)oxy)-4-methylphenyl)-6-(trifluoromethyl)picolinamide $^1$H NMR (400 MHz, DMSO) δ 10.29 (s, 1H), 8.75 (s, 1H), 8.37 (d, J = 8.4 Hz, 2H), 8.18 (d, J = 7.6 Hz, 1H), 7.56 (s, 1H), 7.41 (d, J = 7.3 Hz, 1H), 7.16 (d, J = 7.2 Hz, 1H), 7.02-6.86 (m, 1H), 4.69 (s, 1H), 3.79-3.54 (m, 4H), 2.17 (s, 3H), 2.03 (s, 2H), 1.80 (s, 2H).
Exact Mass (calculated): 474.15; MS (ESI) m/z (M + 1)$^+$: 475.15.

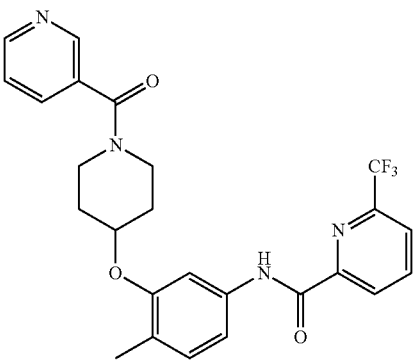 [SMILES: Cc1ccc(NC(=O)c2cccc(C(F)(F)F)n2)cc1OC1CCN(C(=O)c2cccnc2)CC1]

Compound 6

N-(4-methyl-3-(1-nicotinoylpiperid-4-yl)oxy)phenyl)-6-(trifluoromethyl)picolinamide Exact Mass (calculated): 484.17; MS (ESI) m/z (M + 1)$^+$: 485.17.

TABLE 1-continued

Exemplary compounds of the present invention and its characterization data

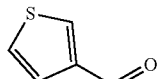
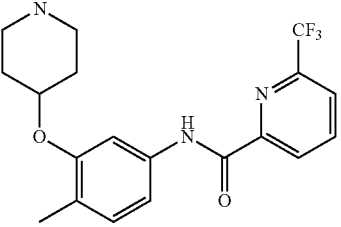

Compound 7

N-(4-methyl-3-((1(thien-3-carbonyl)piperid-4-yl)oxy)phenyl)-6-(trifluoromethyl)picolinamide Exact Mass (calculated): 489.13; MS (ESI) m/z (M + 1)$^+$: 490.13.

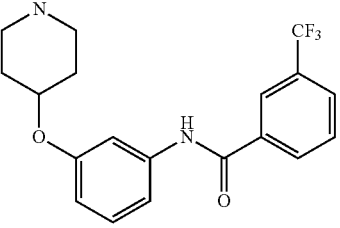

Compound 8

N-(3-((1-acroloylpiperid-4-yl)oxy)phenyl)-3-(trifluoromethyl)benzamide

Exact Mass (calculated): 418.15; MS (ESI) m/z (M + 1)$^+$: 419.15.

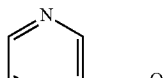
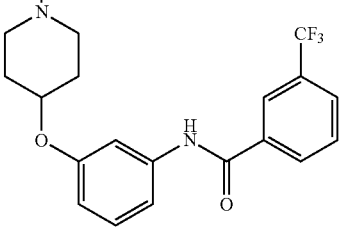

Compound 9

N-(3-((nicotinoylpiperid-4-yl)oxy)phenyl)-3-(trifluoromethyl)benzamide $^1$H NMR (400 MHz, DMSO) δ 10.45 (s, 1H), 8.64 (s, 2H), 8.27 (s, 2H), 8.04-7.69 (m, 3H), 7.50 (s, 1H), 7.48 (s, 1H), 7.34 (s, 1H), 7.27 (s, 1H), 6.78 (s, 1H), 4.64 (s, 1H), 3.95 (s, 1H), 3.52 (s, 2H), 1.98 (s, 2H), 1.70 (s, 2H).
Exact Mass (calculated): 469.16; MS (ESI) m/z (M + 1)$^+$: 470.16.

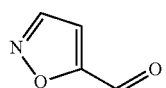
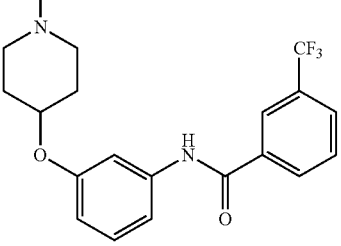

Compound 10

N-(3-((1(isoxazol-5-carbonyl)piperid-4-yl)oxy)phenyl)-3-(trifluoromethyl)benzamide Exact Mass (calculated): 459.14; MS (ESI) m/z (M + 1)$^+$: 460.14.

TABLE 1-continued

Exemplary compounds of the present invention and its characterization data

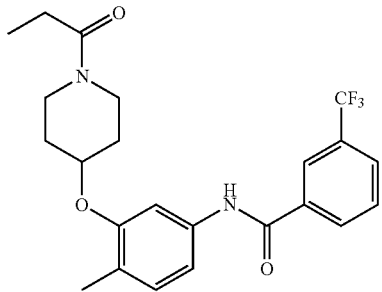 [SMILES: CCC(=O)N1CCC(Oc2cc(NC(=O)c3cccc(C(F)(F)F)c3)ccc2C)CC1]

Compound 11

N-(3-((1-propionylpiperid-4-yl)oxy)-4-methylphenyl)-3-(trifluoromethyl)benzamide $^1$H NMR (400 MHz, DMSO) δ 10.39 (s, 1H), 8.29 (s, 2H), 7.99 (d, J = 7.4 Hz, 1H), 7.81 (t, J = 7.0 Hz, 1H), 7.50 (s, 1H), 7.31 (d, J = 8.0 Hz, 1H), 7.15 (d, J = 7.9 Hz, 1H), 4.57 (s, 1H), 3.68 (s, 2H), 3.44 (s, 2H), 2.37 (m, 2H), 2.16 (s, 3H), 1.95 (s, 2H), 1.68 (s, 2H), 1.02 (m, 3H).
Exact Mass (calculated): 434.18; MS (ESI) m/z (M + 1)$^+$: 435.18.

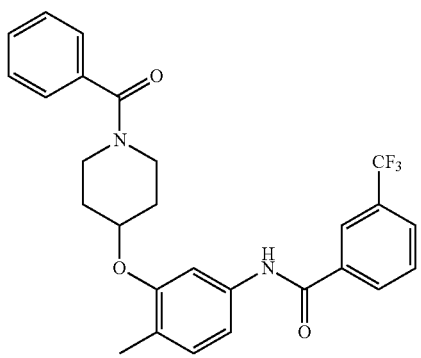 [SMILES: Cc1ccc(NC(=O)c2cccc(C(F)(F)F)c2)cc1OC1CCN(C(=O)c2ccccc2)CC1]

Compound 12

N-(3-(1-benzoylpiperid-4-yl)oxy)-4-methylphenyl)-3-(trifluoromethyl)benzamide $^1$H NMR (400 MHz, DMSO) δ 12.96 (s, 1H), 10.39 (s, 1H), 8.29 (s, 2H), 7.98 (s, 3H), 7.81 (s, 1H), 7.64 (s, 1H), 7.48 (m, 8H), 7.30 (s, 1H), 7.16 (s, 1H), 4.61 (s, 1H), 3.93-3.33 (m, 4H), 2.18 (s, 3H), 2.02 (s, 2H), 1.76 (s, 2H).
Exact Mass (calculated): 482.18; MS (ESI) m/z (M + 1)$^+$: 483.18.

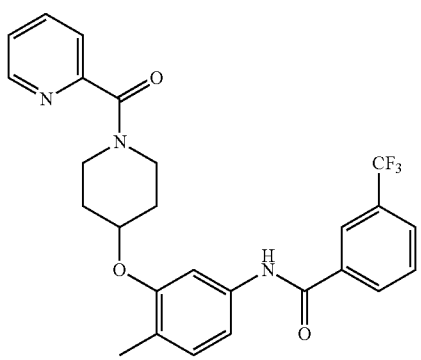 [SMILES: Cc1ccc(NC(=O)c2cccc(C(F)(F)F)c2)cc1OC1CCN(C(=O)c2ccccn2)CC1]

Compound 13

N-(4-methyl-3-((1-pyridin-2-formylpiperid-4-yl)oxy)phenyl)-3-(trifluoromethyl)benzamide $^1$H NMR (400 MHz, DMSO) δ 10.39 (s, 1H), 8.61 (s, 1H), 8.28 (s, 2H), 7.96 (m, 2H), 7.80 (t, J = 7.9 Hz, 1H), 7.61 (d, J = 7.2 Hz, 1H), 7.50 (s, 2H), 7.31 (d, J = 7.7 Hz, 1H), 7.16 (d, J = 8.4 Hz, 1H), 3.96-3.33 (m, 4H), 2.18 (s, 3H), 2.03 (s, 2H), 1.76 (s, 2H).
Exact Mass (calculated): 483.17; MS (ESI) m/z (M + 1)$^+$: 484.17.

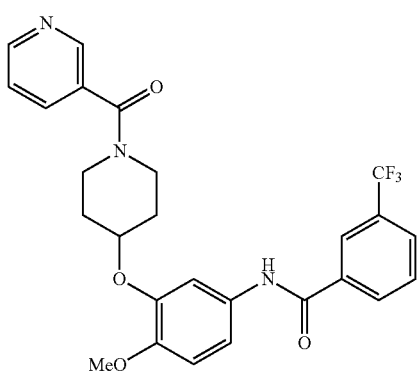 [SMILES: COc1ccc(NC(=O)c2cccc(C(F)(F)F)c2)cc1OC1CCN(C(=O)c2cccnc2)CC1]

Compound 14

N-(4-methoxy-3-(1-nicolinoylpiperid-4-yl)oxy)phenyl)-3-(trifluoromethyl)benzamide Exact Mass (calculated): 499.17; MS (ESI) m/z (M + 1)$^+$: 500.17.

TABLE 1-continued

Exemplary compounds of the present invention and its characterization data

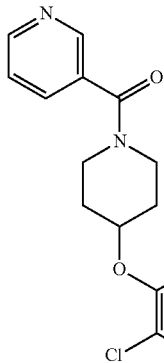

Compound 15

N-(4-chloro-3-(1-nicotinoylpiperid-4-yl)oxy)phenyl)-3-(trifluoromethyl)-benzamide $^1$H NMR (400 MHz, DMSO) δ 10.57 (s, 1H), 8.67 (s, 2H), 8.27 (s, 2H), 8.00 (d, J = 7.4 Hz, 1H), 7.90 (d, J = 7.1 Hz, 1H), 7.82 (t, J = 7.5 Hz, 1H), 7.72 (s, 1H), 7.58-7.38 (m, 3H), 4.71 (s, 1H), 3.91-3.34 (m, 4H), 2.07 (s, 2H), 1.81 (s, 2H).
Exact Mass (calculated): 503.12; MS (ESI) m/z (M + 1)$^+$: 504.12.

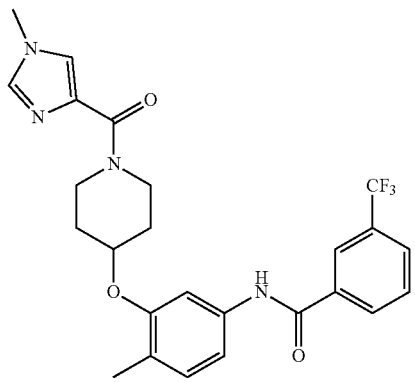 [SMILES: Cc1ccc(NC(=O)c2cccc(C(F)(F)F)c2)cc1OC1CCN(C(=O)c2cn(C)cn2)CC1]

Compound 16

N-(4-methyl-3-((1-(1-methyl-1H-imidazol-4-carbonyl)piperid-4-yl)oxy)phenyl)-3-(trifluoromethyl)benzamide Exact Mass (calculated): 486.18; MS (ESI) m/z (M + 1)$^+$: 487.18.

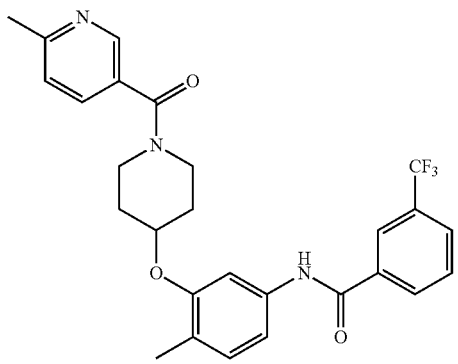 [SMILES: Cc1ccc(C(=O)N2CCC(Oc3cc(NC(=O)c4cccc(C(F)(F)F)c4)ccc3C)CC2)cn1]

Compound 17

N-(4-methyl-3-((1-(2-methylnicotinoyl)piperid-4-yl)oxy)phenyl)-3-(trifluoromethyl)benzamide Exact Mass (calculated): 497.19; MS (ESI) m/z (M + 1)$^+$: 498.19.

TABLE 1-continued

Exemplary compounds of the present invention and its characterization data

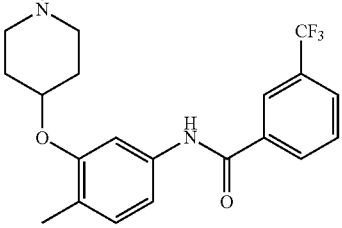

Compound 18

N-(4-methyl-3-((1-(3-methylnicotinoyl)piperid-4-yl)oxy)phenyl)-3-(trifluoromethyl)benzamide Exact Mass (calculated): 486.18; MS (ESI) m/z (M + 1)$^+$: 487.18.

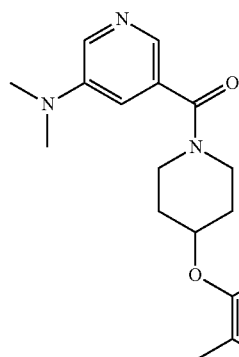

Compound 19

N-(3-((1-(3-(dimethylamino)nicotinoyl)piperid-4-yl)oxy)-4-methylphenyl)-3-(trifluoromethyl)benzamide Exact Mass (calculated): 526.20; MS (ESI) m/z (M + 1)$^+$: 527.20.

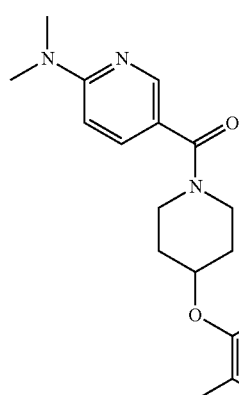

Compound 20

N-(3-((1-(2-(dimethylamino)nicotinoyl)piperid-4-yl)oxy)-4-methylphenyl)-3-(trifluoromethyl)benzamide Exact Mass (calculated): 526.20; MS (ESI) m/z (M + 1)$^+$: 527.20.

EXAMPLE 2

Effects of the Novel Kinase Inhibitor on Cancer Cell Growth

Compounds of the present invention were further evaluated for their activity and selectivity in proliferation inhibition assay of cancer cells, by testing the effect of Compound 4 of the present invention as a C-KIT inhibitor on proliferation of cancer cells, with nilotinib (purchased from Shanghai Haoyuan Chemexpress Co., Ltd.), imatinib (purchased from Shanghai Haoyuan Chemexpress Co., Ltd.), and comparative compounds A, B, and C as controls:

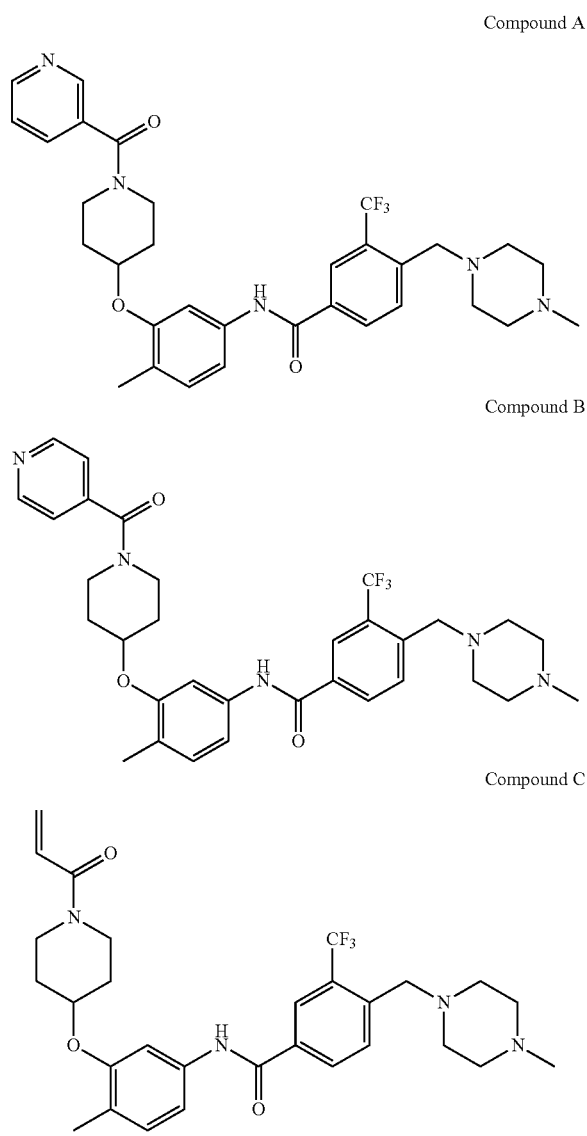

In the present example, the following cells were used: chronic myelogenous leukemia cells K562 (expressing P210 Bcr-Abl mutant gene), human megakaryocytic leukemia cells MEG-01 (expressing P210 Bcr-Abl mutant gene), human peripheral blood basophilic leukemia cells Ku812 (expressing Bcr-Abl mutant gene) (all above cells purchased from ATCC, USA), human gastrointestinal stromal tumor cell lines GIST-T1 cells (expressing wild-type C-KIT gene) (purchased from Cosmo Bio Co., Ltd., Japan), human gastrointestinal stromal tumor cell lines GIST-882 cells (expressing wild-type C-KIT gene) (presented by the Professor Gray Lab, Dana-Farber Cancer Institute, Harvard University, USA), mouse pro-B cells BaF3 (purchased from ATCC, USA).

In addition, in the present example, further uses: mouse P210/BaF3 (stably expressing P210 Bcr-Abl mutant gene), mouse Tel-ABL-BaF3 (stably expressing wild-type ABL kinase), mouse Tel-cKit-BaF3 (stably expressing C-KIT-wild-type kinase), mouse Tel-cKit/V559D-BaF3 (stably expressing C-KIT V559D mutant kinase), mouse Tel-cKit/V559D/V654A-BaF3 (stably expressing C-KIT V559D/V654A mutant kinase), mouse Tel-cKit/N822K-BaF3 (stably expressing C-KIT N822K mutant kinase), mouse Tel-cKit/V654A-BaF3 (stably expressing C-KIT V654A mutant kinase), mouse Tel-cKit/L567P-BaF3 (stably expressing C-KIT L567P mutant kinase), mouse Tel-cKit/T670I-BaF3 (stably expressing C-KIT T670I mutant kinase), mouse Tel-PDGFRα-BaF3 (stably expressing PDGFRα kinase), mouse Tel-PDGFRβ-BaF3 (stably expressing PDGFRβ kinase), mouse Tel-VEGFR2-BaF3 (stably expressing VEGFR2 kinase), mouse Tel-RET-BaF3 (stably expressing RET kinase). The above cell lines were all constructed by our laboratory according to the following method: the kinase region sequences of human P210 Bcr-Abl, ABL, C-KIT, C-KIT V559D, C-KIT V559D/V654A, C-KIT N822K, C-KIT V654A, C-KIT L567P, C-KIT T670I, PDGFRα, PDGFRβ, VEGFR2, RET were amplified respectively by PCR, inserted respectively into MSCV-Puro vectors harboring N-terminal TEL fragment and/or NPM fragment and/or TPR fragment (Clontech), then the vectors were stably transfected into mouse BaF3 cells by retrovirus methods and growth factor IL-3 was removed, eventually obtaining cell lines that are transferred protein (P210 Bcr-Abl, ABL, C-KIT, C-KIT V559D, C-KIT V559D/V654A, C-KIT N822K, C-KIT V654A, C-KIT L567P, C-KIT T670I, PDGFRα, PDGFRβ, VEGFR2, RET)-dependent.

In the example, different concentrations (0.000508 μM, 0.00152 μM, 0.00457 μM, 0.0137 μM, 0.0411 μM, 0.123 μM, 0.370 μM, 1.11 μM, 3.33 μM, 10 μM) of Compound 4 and the control compounds nilotinib, imatinib, the comparative compounds A, B, C (synthesized in the laboratory according to a method similar to Example 1) were added to the above cells respectively. The cells were incubated for 72 hours, and then the number of viable cells was quantified with a microplate reader by using CCK-8 Cell Viability Assay Kit (purchased from Bestbio Company, Shanghai, China) (CCK-8 can be reduced by dehydrogenase in living cells to a highly water-soluble yellow formazan product, and the amount of formazan produced is proportional to the number of living cells). And $GI_{50}$ of Compound and each of the control compounds were calculated (the results are shown in Table 2).

The experimental results shown in Table 2 indicated that Compound 4 of the present invention had no significant inhibitory effect on the proliferation of cells expressing wild-type ABL and mutant Bcr-Abl kinase ($GI_{50}$ was greater than 5 μM), and had a significant inhibitory effect on the proliferation of cells expressing wild-type C-KIT kinase ($GI_{50}$ was less than 0.5 μM). Such results indicated that, with regard to ABL kinase (wild-type or mutant) and C-KIT kinase (wild-type or mutant), Compound 4 of the present invention selectively and effectively inhibited C-KIT kinase.

In contrast, in the same experiment, the control compounds nilotinib, imatinib, and the comparative compounds B and C had significant inhibitory effects not only on the proliferation of cells expressing C-KIT kinase ($GI_{50}$ was less than 0.5 µM), but also on proliferation of cells expressing wild-type ABL and mutant Bcr-Abl kinase. Such results indicated that the control compounds nilotinib, imatinib, the comparative compounds B and C had similar inhibition for ABL kinase (wild-type or mutant) and C-KIT kinase (wild-type or mutant), in other words, the above four control compounds showed poor selectivity.

The above comparison showed that Compound 4 of the present invention exhibited C-KIT kinase selectivity superior to the control compounds nilotinib, imatinib, the comparative compounds B and C.

In addition, the results in Table 2 also reflected the inhibitory effect of Compound 4 of the present invention on cells expressing mutant C-KIT kinase (for example, Tel-cKit/V559D-BaF3 cells). Since the drug resistance occurred in the treatment of gastrointestinal stromal tumor (GIST) may be related to the mutation of C-KIT kinase, the results of the present Example revealed the possibility using Compound 4 of the present invention for the second-stage treatment of GIST patients, which helps to solve the problem of C-KIT kinase mutation-related resistance occurred in GIST patients after the administration.

tein kinase, Bcr-Abl fusion protein and other protein kinases closely related to these proteins, such as Stat5, AKT, ErK, S6K, S6, PDGFRα, and the like in the cells were evaluated, by measuring multiple cellular biochemical endpoints and functional endpoints.

Both of gastrointestinal stromal tumor cell lines GIST-T1 and GIST-882 were treated with different concentrations of 0 µM, 0.03 µM, 0.1 µM, 0.3 µM, 1 µM, 3 µM, 10 µM of Compound 4 and 1 µM of the control compound imatinib for 2 hours; Chronic Myelogenous Leukemia cells K562 (expressing P210 Bcr-Abl mutant gene) was treated with different concentrations of 0 µM, 0.01 µM, 0.03 µM, 0.1 µM, 0.3 µM, 1 µM, 3 µM of Compound 4, the comparative compound A and 1 µM of the control compound imatinib, 0.1 µM of the control compound dasatinib for 2 hours; samples were collected. The effects of Compound 4, and the comparative compound A, imatinib, and dasatinib on phosphorylation of proteins such as C-KIT, Stat5, AKT, ErK, S6K, S6, and PDGFRα in the cells were determined. The results were shown in FIG. 1.

The results showed that, in gastrointestinal stromal tumor cell lines GIST-T1 (expressing C-KIT gene) and human

TABLE 2

Effects of different inhibitors on cancer cell growth (results shown as $GI_{50}$ values in µM)

| Cell name | Gene expression | nilotinib | imatinib | Compound A | Compound B | Compound C | Compound 4 |
|---|---|---|---|---|---|---|---|
| K562 | P210 Bcr-Abl | 0.003 | 0.267 | 0.056 | 0.07 | 0.28 | >10 |
| MEG-01 | P210 Bcr-Abl | 0.0004 | 0.074 | 0.018 | 0.034 | 0.108 | 7.43 |
| Ku812 | Bcr-Abl | 0.0012 | 0.163 | 0.057 | 0.236 | 0.19 | 6.71 |
| P210/BaF3 | Bcr-Abl | 0.0125 | 0.27 | 0.164 | | 0.99 | 6.05 |
| Tel-ABL-BaF3 | ABL WT | 0.026 | 0.4 | 0.145 | 0.146 | 0.42 | 5.06 |
| Tel-cKit-BaF3 | KIT WT | 0.047 | 0.412 | 0.147 | 0.17 | 0.16 | 0.19 |
| GIST-T1 | KIT WT | 0.006 | 0.008 | 0.014 | 0.027 | 0.03 | 0.021 |
| GIST-882 | KIT WT | 0.017 | 0.014 | 0.067 | | | 0.043 |
| Tel-cKit/V559D-BaF3 | KIT V559D | 0.022 | 0.039 | 0.134 | 0.02 | 0.036 | 0.04 |
| Tel-cKit/V559D/V654A-BaF3 | KIT V559D/V654A | 0.648 | 3.0 | 2.45 | | | 1.05 |
| Tel-cKit/N822K-BaF3 | KIT N822K | 0.166 | 1.29 | 0.378 | 0.13 | 0.38 | 0.94 |
| Tel-cKit/V654A-BaF3 | KIT V654A | 0.365 | 2.49 | 2.26 | 0.585 | 0.401 | 1.03 |
| Tel-cKit/L576P-BaF3 | KIT L576P | 0.081 | 0.102 | 0.321 | | | 0.148 |
| Tel-cKit/T670I-BaF3 | KIT T670I | 2.86 | 6.67 | 1.01 | 0.427 | 0.952 | 5.31 |
| Tel-RET-BaF3 | RET WT | 2.66 | 6.31 | 0.39 | 0.3 | 0.49 | 0.59 |
| Tel-PDGFRα-BaF3 | PDGFRα | 0.032 | 0.034 | 0.095 | 0.015 | 0.036 | 0.038 |
| Tel-PDGFRβ-BaF3 | PDGFRβ | 0.032 | 0.019 | 0.052 | 0.04 | 0.042 | 0.027 |
| Tel-VEGFR2-BaF3 | VEGFR2 | 5.38 | >10 | 0.017 | 0.007 | 0.005 | 0.347 |
| BaF3 | | >10 | >10 | >10 | >10 | >10 | >10 |

EXAMPLE 3

Effects of Compound 4, Comparative Compound A, Imatinib and Dasatinib on Cell Signaling Pathways, Respectively In three cell lines of human stromal tumors cell lines GIST-T1 (expressing wild-type C-KIT gene), human gastrointestinal stromal tumor cell lines GIST-882 (expressing wild-type C-KIT gene), and Chronic Myelogenous Leukemia cells K562 (expressing P210 Bcr-Abl mutant gene), the effects of Compound 4, and the comparative compound A, imatinib, dasatinib (purchased from Shanghai Haoyuan Chemexpress Co., Ltd.) on phosphorylation of C-KIT pro-gastrointestinal stromal tumor cell lines GIST-882 (expressing C-KIT gene), Compound 4 with the concentration of 0.1 µM was capable of significantly inhibiting the phosphorylation of C-KIT oncogenic protein and also had a significant inhibitory effects on the phosphorylation of proteins such as Stat5, AKT, ErK, S6K, S6, PDGFRα and the like in key signaling pathways in the cells. In this experiment, the control compound imatinib also showed similar inhibition of phosphorylation.

In Chronic Myelogenous Leukemia cell lines K562 (expressing P210 Bcr-Abl mutant gene), Compound 4 with the concentration up to 3 µM had no effect on the phosphorylation of Bcr-Abl kinase, and also had no effect on the phosphorylation of proteins such as AKT, ErK in key signaling pathways in the cells. In the same experiment, the control compound dasatinib with the concentration of 0.1 µM strongly inhibited the phosphorylation of Bcr-Abl kinase, and also had very strong inhibitory effects on proteins correlated in its signaling pathways upstream and downstream. The control compound imatinib with the concentration of 1 µM exhibited an inhibitory effect on the phosphorylation of Bcr-Abl kinase. The comparative compound A with the concentration of 0.1 µM had a very strong inhibitory effect on the phosphorylation of Bcr-Abl kinase, and also had very strong inhibitory effects on proteins related in its signaling pathways upstream and downstream.

These results suggested that both Compound 4 and imatinib played a role in C-KIT-related signaling pathways, and they were possible to affect the cell proliferation of gastrointestinal stromal tumor GIST-T1 cells and GIST-882 cells carrying C-KIT oncogenic protein by inhibiting the phosphorylation of the oncogenic protein C-KIT. Meanwhile, Compound 4 of the present invention had no or little effect on phosphorylation of Bcr-Abl kinase, indicating that Compound 4 of the present invention had good C-KIT inhibition selectivity and lower toxic side effects.

EXAMPLE 4

Effects of Compound 4 and Imatinib on Apoptosis, Respectively

Figure 2:
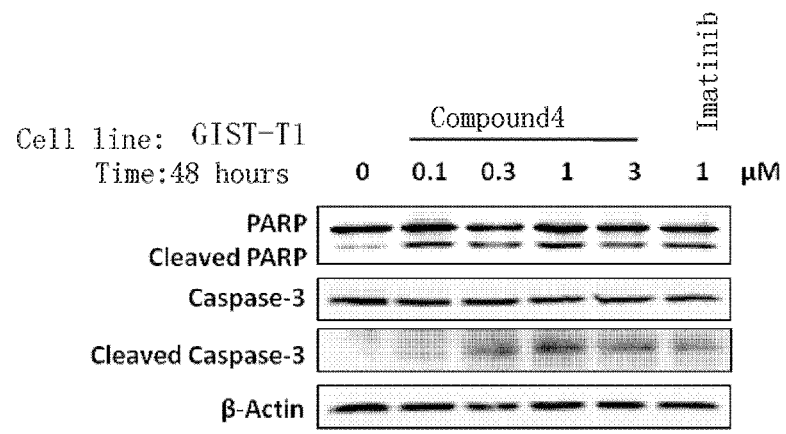
FIGS. 2a and 2b illustrate the effects of Compound 4 and imatinib on the apoptosis of human gastrointestinal stromal tumor cells GIST-T1 and human gastrointestinal stromal tumor cells GIST-882, respectively.
Figure 2:
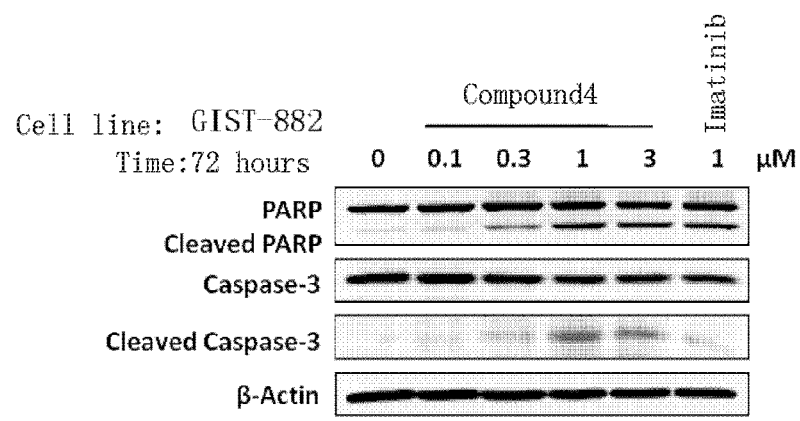

The effects of Compound 4 on protein cleavage of DNA repairase poly(ADP-ribose) polymerase (PARP) and Caspase (cysteinyl aspartate-specific proteinase) 3 that were closely related to cell apoptosis were examined in gastrointestinal stromal tumor cell lines GIST-T1 (expressing wild-type C-KIT gene) and human gastrointestinal stromal tumor cell lines GIST-882 (expressing wild-type C-KIT gene), in order to study whether cell death after the administration was caused by apoptosis or necrosis. Gastrointestinal stromal tumor cell lines GIST-T1 and gastrointestinal stromal tumor cell lines GIST-882 cells were treated with different concentrations of 0 µM, 0.1 µM, 0.3 µM, 1 µM, 3 µM of Compound 4 and 1 µM of the control compound imatinib, and then after 48 and 72 hours, the cells were collected. The effects of different concentrations of drugs on protein cleavage of DNA repairase poly(ADP-ribose) polymerase (PARP) and Caspase (cysteinyl aspartate-specific proteinase) 3 at different periods of time were examined by Western Blot. The results were shown in FIGS. 2a and 2b.

The results suggested that, when the concentration of Compound 4 was 0.3 µM, significant cleavage of DNA repairase poly(ADP-ribose) polymerase (PARP) and cleavage of Caspase 3 that is downstream of PARP were observed both in gastrointestinal stromal tumor cell lines GIST-T1 (expressing C-KIT gene) administrated 48 hours later and human gastrointestinal stromal tumor cell lines GIST-882 (expressing C-KIT gene) administrated 72 hours later. For the experimental group with 1 µM imatinib, significant cleavage of DNA repairase poly(ADP-ribose) polymerase (PARP) and cleavage of Caspase 3 that is downstream of PARP were also observed. These indicated that the cell deaths caused after treating the cells with Compound 4 and imatinib were by apoptosis, and not necrosis. In other words, Compound 4 and imatinib could induce apoptosis of gastrointestinal stromal tumor cell lines GIST-T1 and GIST-882 expressing C-KIT oncogenic protein.

EXAMPLE 5

Effects of Compound 4 and Imatinib on Cell Cycles, Respectively

Effects of Compound 4, imatinib and sunitinib (purchased from Shanghai Haoyuan Chemexpress Co., Ltd.) on cell cycle distribution were examined respectively in gastrointestinal stromal tumor cell lines GIST-T1 (expressing wild-type C-KIT gene) and human gastrointestinal stromal tumor cell lines GIST-882 (expressing wild-type C-KIT gene), in order to study the growth cycle to which the cells were blocked upon compound administration.

Figure 3:
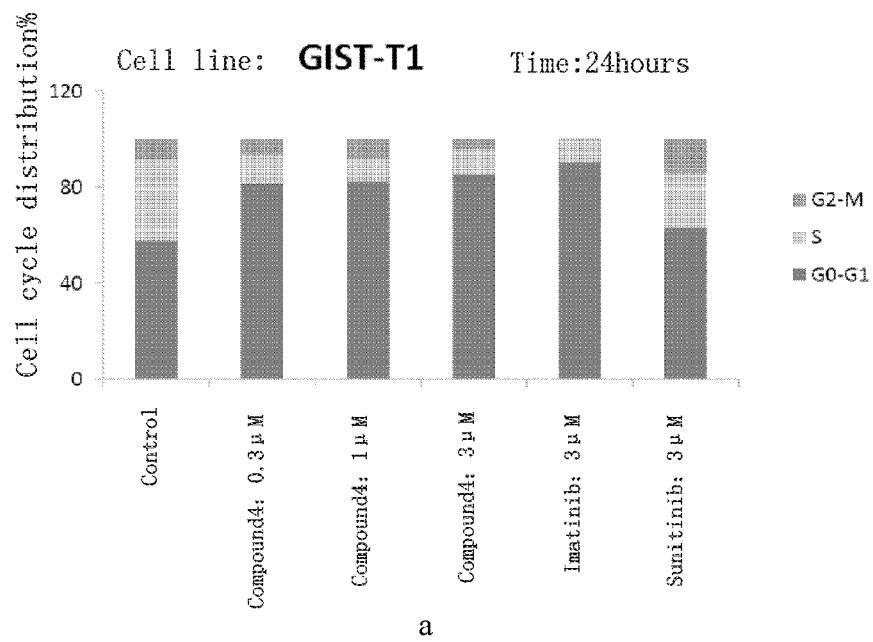
FIGS. 3a and 3b illustrate the effects of Compound 4, imatinib and sunitinib on the cell cycles of human gastrointestinal stromal tumor cells GIST-T1 and human gastrointestinal stromal tumor cells GIST-882, respectively.
Figure 3:
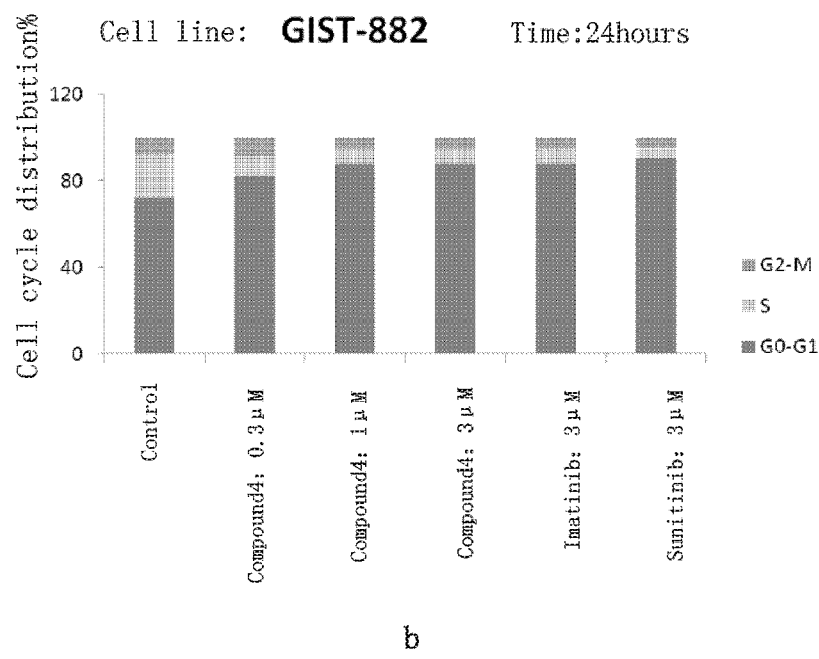

The above cells were treated with different concentrations (0 µM, 0.3 µM, 1 µM, 3 µM in DMSO) of Compound 4, 3 µM (in DMSO) of control compound imatinib and 3 µM (in DMSO) of control compound sunitinib for 24 or 48 hours, and then cells were collected and washed twice with 1× PBS buffer, and fixed with 75% ethanol at −20° C. for 24 hours, washed again with 1× PBS buffer twice, followed by addition of 0.5 mL 1× PBS buffer and 0.5 mL of PI dyeing liquor (purchased from BD Bioscience, USA), and then the cells were placed in the dark at 37° C. to dye for 15 minutes and the cell cycle distribution was detected by flow cytometry (BD FACS Calibur). The results were shown in FIGS. 3a and 3b.

The results showed that, Compound 4 had significant effects on the cell cycles of two cells, gastrointestinal stromal tumor cell lines GIST-T1 (expressing C-KIT gene) cells treated 24 hours later, and human gastrointestinal stromal tumor cell lines GIST-882 (expressing C-KIT gene) cells treated 48 hours later, such that the cell cycles of both cells were significantly blocked in the G0-G1 phase.

EXAMPLE 6

Detection of In Vitro Inhibition Activity (Enzymatic Activity) of Compound 4

The $IC_{50}$ value of Compound 4 against protein kinase C-KIT was determined in an in vitro enzyme activity assay. The kinase domain of protein kinase C-KIT was cloned into the insect expression vector pFASTHTA (purchased from Invitrogen life technologies), and the protein with His tag was expressed using the insect expression system Bac-to-Bac Baculovirus Expression System (purchased from Invitrogen life technologies). The constructed vector was transfected into SF9 packaging virus (purchased from Invitrogen life technologies), and the virus was used to infect SF9 to express the protein. Purification was performed using affinity chromatography.

9 µL (6 ng/µL) of purified C-KIT protein kinase was reacted with 1 µL of the above Compound 4 with 3× gradient dilution (the final concentrations of the drug were 10 µM, 3 µM, 1 µM, 0.3 µM, 0.1 µM, 0.03 µM, 0.01 µM, 0.003 µM) at room temperature for 4 hours;

2 µL of ATP and 3 µL of substrate, Poly(4:1 Glu, Tyr) Peptide (Promega, US), were added (final concentrations were 10 µM and 0.2 µg/µL, respectively), and reacted at 37° C. for 1 hour;

5 μL of ADP-Glo™ (Promega, US) was added into 5 μL of reacted kinase solution and reacted at room temperature for 40 min, to stop the kinase reaction and consume the remained ATP;

10 μL of kinase detection reagent was added to transfer ADP into ATP, and the newly synthesized ATP was detected by using coupled luciferase/fluorescein reaction, then the $IC_{50}$ values were calculated by using a plotting method based on the Envision reading.

Figure 4:
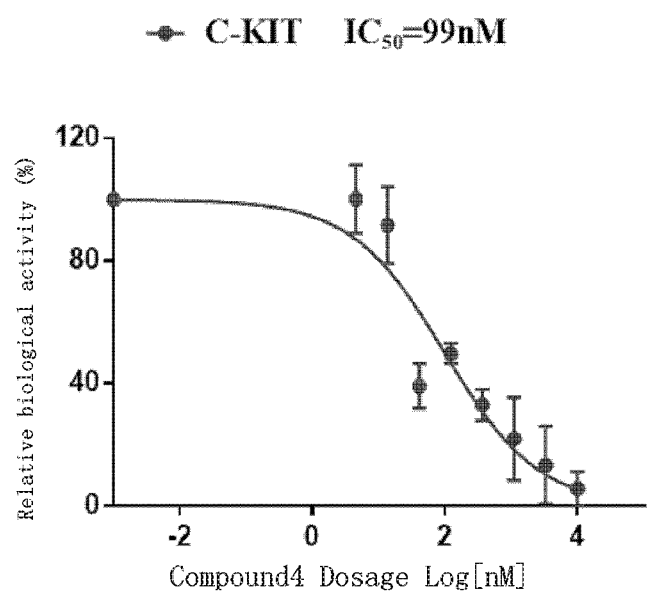
FIG. 4 illustrates the experimental result of in vitro inhibitory activity of Compound 4 against C-KIT kinase.

The experiment results were shown in FIG. 4. Compound 4 of the present invention had strong inhibitory effect on C-KIT protein kinase, with $IC_{50}$ value of 99 nM. The results demonstrated that Compound 4 of the present invention was an effective C-KIT kinase inhibitor.

EXAMPLE 7

Experimental Results of Compound 4 and Control Compound Imatinib in Mouse Models of Gastrointestinal Stromal Tumor Cell Lines GIST-T1 and Gastrointestinal Stromal Tumor Cell Lines GIST-882

1. 4-6 week-old Bal b/c female mice were purchased from Shanghai SLAC Experimental Animal Co., Ltd., and were raised in a SPF-level laboratory. Drinking water and padding were both subjected to aseptic processing via high-pressure disinfection, and all operations of the mice were conducted under aseptic conditions;

2. About $5×10^6$ gastrointestinal stromal tumor cell lines GIST-T1 or GIST-882 (purchased from ATCC) were respectively injected subcutaneously at left side back of all mice at Day 0;

3. Methyl cellulose (HKI) solvent (6 mice); Compound 4 at a dosage of 25 mg/kg mouse weight (6 mice); Compound 4 at a dosage of 50 mg/kg mouse weight (6 mice); Compound 4 at a dosage of 100 mg/kg mouse weight (6 mice); the control compound imatinib at a dosage of 100 mg/kg mouse weight (6 mice) were orally administrated to corresponding mice daily from Day 15;

4. Length/width of subcutaneous tumors were measured daily with a vernier caliper from Day 15 and mice weight was recorded daily to determine the effects of Compound 4 and the control compound imatinib on mice weight;

5. Mice were sacrificed on Day 36 (for GIST-882 mouse model) or Day 43 (GIST-T1 mouse model) and subcutaneous tumors were taken out and weighed for comparison;

6. Tumor tissue specimens were prepared into protein lysate samples for further usage;

7. Growth trend of subcutaneous tumors from Day 16 to Day 43 was derived, and tumor volume was calculated as length×width×width/2 $mm^3$.

The experimental results were shown in FIGS. 5a-5b and 5e-5f. In mouse tumor model of gastrointestinal stromal tumor cell lines GIST-T1, Compound 4 administrated at a dosage of 25 mg/kg had exhibited certain inhibitory effect on mouse tumors on Day 4 after administration, and the inhibitory effect of Compound 4 on mouse tumors was more and more significant with the increase in the dosage and the administrated days. For the group of Compound 4 administrated at a dosage of 50 mg/kg, the tumor inhibition rates could reach 65.3% and 44% in mouse models of gastrointestinal stromal tumor cell lines GIST-T1 on Day 28 after administration, and in mouse models of gastrointestinal stromal tumor cell lines GIST-882 on Day 21 after administration, respectively; For the group of Compound 4 administrated at a dosage of 100 mg/kg, the tumor inhibition rates could reach 73.8% and 58% in mouse models of gastrointestinal stromal tumor cell lines GIST-T1 and gastrointestinal stromal tumor cell lines GIST-882, respectively. In the same experiment, For the group of the control compound imatinib administrated at a dosage of 100 mg/kg, the tumor inhibition rates could reach 72.4% and 49% in mouse models of gastrointestinal stromal tumor cell lines GIST-T1 on Day 28 after administration and in mouse models of gastrointestinal stromal tumor cell lines GIST-882 on Day 21 after administration, respectively. This indicated that the effects of Compound 4 of the present invention were superior to that of the control compound imatinib in animal models.

Figure 5:
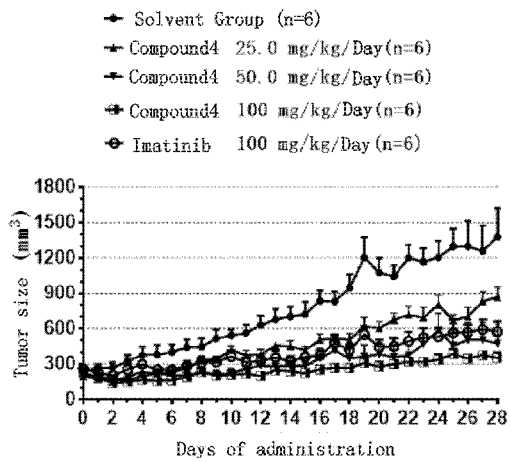
Figure 5:
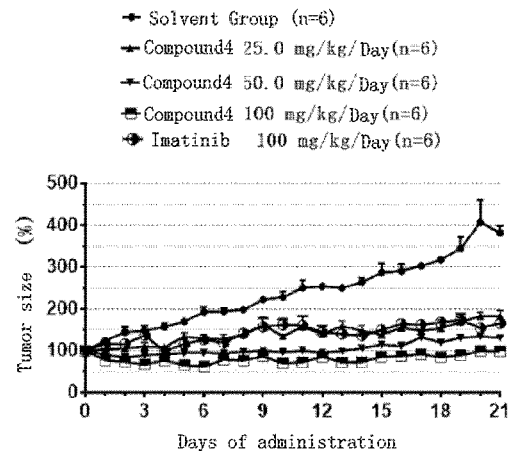
Figure 5:
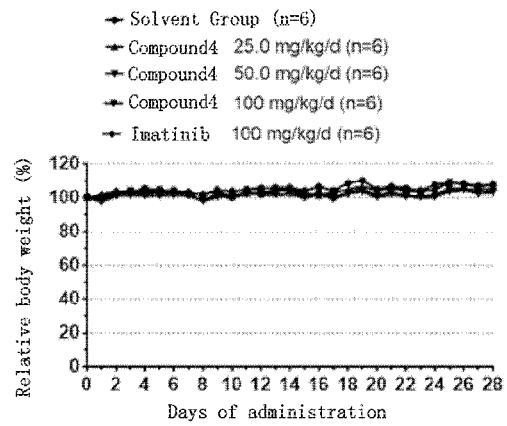
Figure 5:
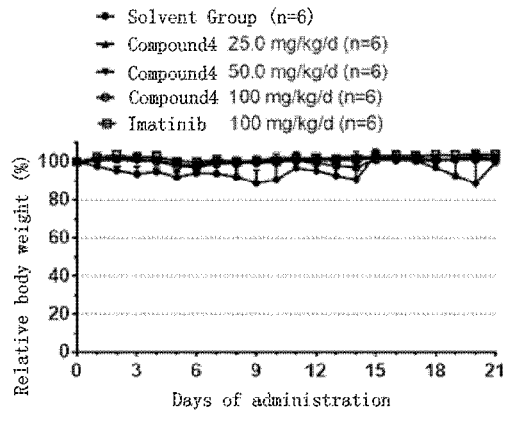
Figure 5:
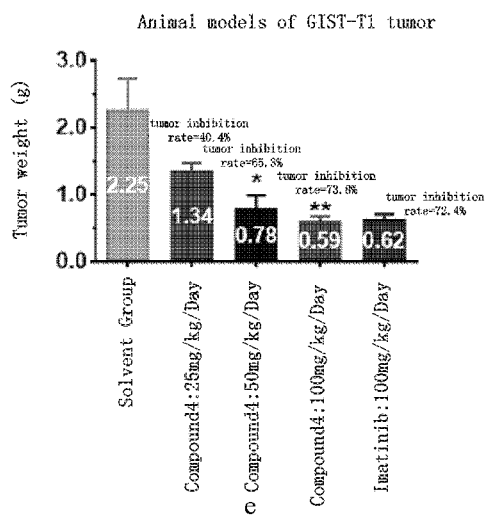
Figure 5:
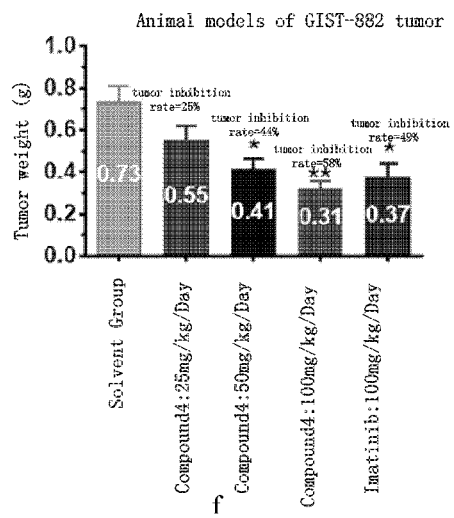

In addition, in combination with the results of FIGS. 5c-5d, it was shown that Compound 4 not only effectively inhibited the growth of mouse tumors, but also had no effect on the body weight of mice, indicating that Compound 4 could be suitable for administration to animals.

EXAMPLE 8

Acute Toxicity Assay in Mouse Models of Gastrointestinal Stromal Tumor Cell Lines GIST-T1

1. 4-6 week-old Bal b/c female mice were purchased from Shanghai SLAC Experimental Animal Co., Ltd., and were raised in a SPF-level laboratory. Drinking water and padding were both subjected to aseptic processing via high-pressure disinfection, and all operations of the mice were conducted under aseptic conditions; 10 healthy mice were selected, and were balanced and randomly divided into 5 groups according to their weights.

2. Specific Information for Administration

Route of administration: oral gavage

Times of administration: 1 time

Observation period: 7 days.

3. Observation Indicators 3.1. Weight

Weighing frequency: upon grouping, the day of administration (D0) to the seventh day after administration (D7). Based on the mouse weight on D0 (starting value of 100%), the graph of the relative body weight over time was plotted.

3.2. Clinical Symptoms Observation

Strict observation was carried out within 4 hours after administration, and then observation was carried out twice a day for a total of 7 days. Observation was carried out and abnormal symptoms or phenomena in each of animals were recorded.

3.3. Number of Deaths

The number of animals died in each of dosage groups during the observation period.

4. Analysis of Results

Comprehensive determination was performed based on animal mortality, clinical symptoms and body weights.

The experimental results were shown in Table 3. When Compound 4 was administrated at a dosage of 1000 mg/kg, there was no significant effect on mouse weight, and no mouse died. When Compound 4 was administrated at a dosage of 2000 mg/kg, the weight of mice decreased slightly, and no mouse died. The mouse was dissected after 7 days, and it was found that there were no obvious abnormalities in the mouse organs. This demonstrated that Compound 4 of the present invention had less toxic side effects; the maximum tolerated dosage of Compound 4 for the mouse was 2000 mg/kg.

In the same experiment, when the comparative compound A was administrated at a dosage of 1000 mg/kg, the mice started to be quiet and lie down around 40 minutes; 1 mouse died on Day 1; and when the comparative compound A was administrated at a dosage of 2000 mg/kg, the gait of mice was unstable after administration; 2 mice died on Day 1. This indicates that Compound 4 of the present invention had less toxic side effects, compared with the compound A.

TABLE 3

| | Groups | Test sample | Dosage (mg/kg) | Concentration (mg/ml) | Administration voluble (ml/kg) | Number of death (number of death/ number of animals in each group) |
|---|---|---|---|---|---|---|
| | \multicolumn{6}{c}{Information about animal death in acute toxicity assay for mice gavaged with single dose of Compound 4} | | | | | |
| 1 | (Negative control group) | Sterilized water for injection | 0 | 0 | 10 | ♀: 0/2: |
| 2 | (Dosage 2000 mg/kg) | Compound 4 solution | 2000 | 200 | 10 | ♀: 0/2: |
| 3 | (Dosage 1000 mg/kg) | Compound 4 solution | 1000 | 100 | 10 | ♀: 0/2: |
| 4 | (Dosage 500 mg/kg) | Compound 4 solution | 500 | 50 | 10 | ♀: 0/2: |
| S | (Dosage 250 mg/kg) | Compound 4 solution | 250 | 25 | 10 | ♀: 0/2: |
| | \multicolumn{6}{c}{Information about animal death in acute toxicity assay for mice gavaged with single dose of Compound A} | | | | | |
| 1 | (Negative control group) | Sterilized water for injection | 0 | 0 | 10 | ♀: 0/2 |
| 2 | (Dosage 2000 mg/kg) | Compound A solution | 2000 | 200 | 10 | ♀: 2/2 |
| 3 | (Dosage 1000 mg/kg) | Compound A solution | 1000 | 100 | 10 | ♀: 1/2 |
| 4 | (Dosage 500 mg/kg) | Compound A solution | 500 | 50 | 10 | ♀: 0/2 |
| 5 | (Dosage 250 mg/kg) | Compound A solution | 250 | 25 | 10 | ♀: 0/2 |

INDUSTRIAL APPLICABILITY

The present invention provides a selective inhibitor of C-KIT kinase, which can be used for inhibiting the activity of C-KIT kinase, or for the treatment, prevention or amelioration of a disease, disorder, or condition, which is modulated or otherwise affected by C-KIT activity, or in which C-KIT activity is implicated. Therefore, it can be prepared as corresponding medicament and has industrial applicability.

While the present invention has been described in detail herein, the present invention is not limited thereto and modifications may be made by those skilled in the art based on the principles of the present invention, and thus, all modifications in accordance with the principles of the present invention are to be understood as within the protection scope of the present invention.

The invention claimed is:

1. A compound of formula (I), or a pharmaceutically acceptable salt thereof:

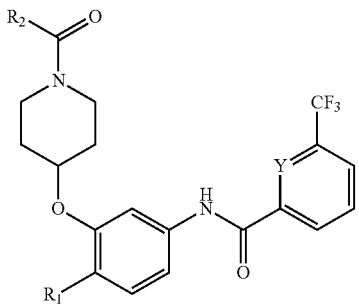

Formula (I)

wherein,
Y is CH;
$R_1$ is selected from the group consisting of H, $C_{1-6}$ alkyl, $C_{1-6}$ alkoxy and halogen;
$R_2$ is pyridinyl optionally substituted with $R_3$;
$R_3$ is selected from the group consisting of $C_{1-6}$ alkyl and $C_{1-6}$ alkylamino.

2. The compound, or a pharmaceutically acceptable salt thereof, as claimed in claim 1, wherein $R_1$ is selected from the group consisting of H, methyl, methoxy, and chloro.

3. The compound, or a pharmaceutically acceptable salt thereof, as claimed in claim 1, wherein $R_1$ is methyl.

4. The compound, or a pharmaceutically acceptable salt thereof, as claimed in claim 1, wherein $R_3$ is selected from the group consisting of methyl and dimethylamino.

5. The compound, or a pharmaceutically acceptable salt thereof, as claimed in claim 1, wherein $R_2$ is selected from the group consisting of 2-pyridinyl, 3-pyridinyl, and 4-pyridinyl.

6. The compound, or a pharmaceutically acceptable salt thereof, as claimed in claim 1, which is selected from the group consisting of the following compounds:

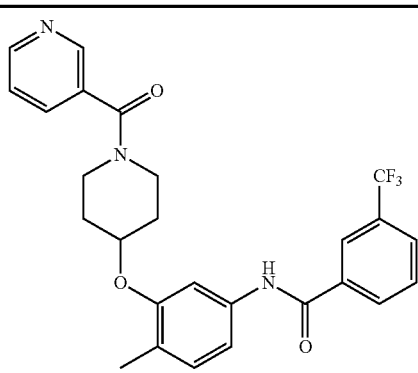

N-(4-methyl-3-(1-nicotinoylpiperid-4-yl)oxy)phenyl)-3-(trifluoromethyl)benzamide Compound 2

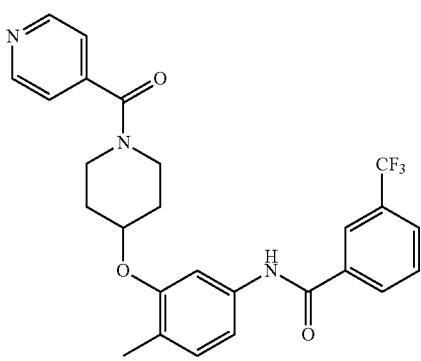 [SMILES: Cc1ccc(NC(=O)c2cccc(C(F)(F)F)c2)cc1OC1CCN(C(=O)c2ccncc2)CC1]

N-(4-methyl-3-(1-isonicotinoylpiperid-4-yl)oxy)phenyl)-3-(trifluoromethyl)benzamide Compound 4

-continued
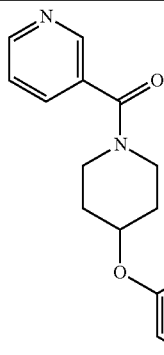
Compound 9
N-(3-((nicotinoylpiperid-4-yl)oxy)phenyl)-3-(trifluoromethyl)benzamide
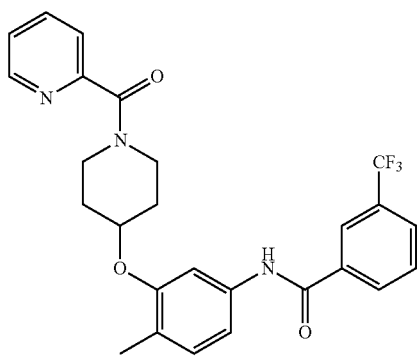 [SMILES: Cc1ccc(NC(=O)c2cccc(C(F)(F)F)c2)cc1OC1CCN(C(=O)c2ccccn2)CC1]
Compound 13
N-(4-methyl-3-((1-pyridin-2-formylpiperid-4-yl)oxy)phenyl)-3-(trifluoromethyl)benzamide
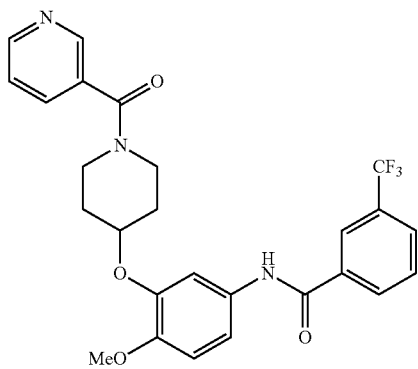 [SMILES: COc1ccc(NC(=O)c2cccc(C(F)(F)F)c2)cc1OC1CCN(C(=O)c2cccnc2)CC1]
Compound 14
N-(4-methoxy-3-(1-nicotinoylpiperid-4-yl)oxy)phenyl)-3-(trifluoromethyl)-benzamide
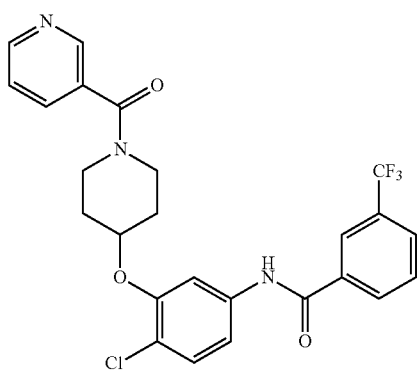 [SMILES: O=C(Nc1ccc(Cl)c(OC2CCN(C(=O)c3cccnc3)CC2)c1)c1cccc(C(F)(F)F)c1]
Compound 15
N-(4-chloro-3-(1-nicotinoylpiperid-4-yl)oxy)phenyl)-3-(trifluoromethyl)-benzamide 7. A pharmaceutical composition, comprising the compound, or a pharmaceutically acceptable salt thereof, as claimed in claim 1, and a pharmaceutically acceptable carrier or excipient.

8. A method for the treatment or amelioration of a gastrointestinal stromal tumor, comprising administering an effective amount of the compound, or a pharmaceutically acceptable salt thereof, as claimed in claim 1.

* * * * *